US012708513B2

(12) United States Patent
Argento et al.

(10) Patent No.: US 12,708,513 B2
(45) Date of Patent: Aug. 18, 2026

(54) PROSTHETIC CARDIAC VALVE SENSOR DEVICES, SYSTEMS, AND METHODS WITH IMAGING

(71) Applicant: Shifamed Holdings, LLC, Campbell, CA (US)

(72) Inventors: Claudio Argento, Felton, CA (US); Andrew Backus, Santa Cruz, CA (US); Alice Yang, Campbell, CA (US); Tom Saul, Portland, OR (US); Ali Salahieh, Saratoga, CA (US)

(73) Assignee: Shifamed Holdings, LLP, Campbell, CA (US)

( * ) Notice: Subject to any disclaimer, the term of this patent is extended or adjusted under 35 U.S.C. 154(b) by 513 days.

(21) Appl. No.: 18/246,311

(22) PCT Filed: Sep. 22, 2021

(86) PCT No.: PCT/US2021/051488
§ 371 (c)(1),
(2) Date: Mar. 22, 2023

(87) PCT Pub. No.: WO2022/066720
PCT Pub. Date: Mar. 31, 2022

(65) Prior Publication Data

US 2023/0363907 A1 Nov. 16, 2023

Related U.S. Application Data

(60) Provisional application No. 63/081,843, filed on Sep. 22, 2020.

(51) Int. Cl.
*A61F 2/24* (2006.01)
*G06T 7/00* (2017.01)

(52) U.S. Cl.
CPC .......... *A61F 2/2442* (2013.01); *G06T 7/0012* (2013.01); *G06T 2207/30048* (2013.01)

(58) Field of Classification Search
CPC .................. A61F 2/2454; A61F 2/2457; A61F 2/2442–2/2448; A61F 2/2463–2/2472;
(Continued)

(56) References Cited

U.S. PATENT DOCUMENTS

| | | |
|---|---|---|
| 363,130 A | 5/1887 | Field |
| 2,728,444 A | 12/1955 | Richardson et al. |

(Continued)

FOREIGN PATENT DOCUMENTS

| | | |
|---|---|---|
| AU | 2012261727 B2 | 10/2015 |
| AU | 2019246822 B2 | 8/2020 |

(Continued)

OTHER PUBLICATIONS

Schaefer; Large heart valves—small heart valves; ISMAAP; Oct. 19, 2015; 5 pages; retrieved from the internet (https://www.ismaap.org/condition-detail/large-heart-valves-small-heart-valves/) on Mar. 21, 2023.

(Continued)

*Primary Examiner* — Alvin J Stewart
(74) *Attorney, Agent, or Firm* — Shay Glenn LLP

(57) ABSTRACT

A method for treating a diseased native valve in a patient includes advancing a distal end of a delivery device that is detachable coupled to an anchor to a first side of a native valve, deploying the anchor from a delivery configuration to a deployed configuration on the first side of the native valve, advancing the anchor in the deployed configuration from the first side of the native valve to a second side of the native valve such that the anchor is located only on the second side of the native valve, rotating the anchor in the deployed configuration around chordae of the native valve, confirming (Continued)

a position of the anchor with an imaging source, and releasing the anchor from the distal end of the delivery device.

16 Claims, 14 Drawing Sheets

(58) Field of Classification Search
CPC .... A61F 2/2475–2/2478; A61F 2/2412; A61B 5/065; A61B 8/0833; A61B 5/4851; A61B 1/05–1/053; A61B 1/00101
See application file for complete search history.

(56) References Cited

U.S. PATENT DOCUMENTS 4,602,911 A 7/1986 Ahmadi et al.
4,605,911 A 8/1986 Jin
4,725,274 A 2/1988 Lane et al.
5,002,563 A 3/1991 Pyka et al.
5,135,844 A 8/1992 Bagchi
5,201,880 A 4/1993 Wright et al.
5,327,905 A 7/1994 Avitall
5,356,424 A 10/1994 Buzerak et al.
5,370,685 A 12/1994 Stevens
5,582,616 A 12/1996 Bolduc et al.
5,662,704 A 9/1997 Gross
5,716,397 A 2/1998 Myers
5,755,601 A 5/1998 Jones
5,778,668 A 7/1998 Adleff
5,779,669 A 7/1998 Haissaguerre et al.
5,873,835 A 2/1999 Hastings et al.
5,944,690 A 8/1999 Falwell et al.
5,997,526 A 12/1999 Giba et al.
6,008,476 A 12/1999 Neiconi
6,048,339 A 4/2000 Zirps et al.
6,053,873 A 4/2000 Govari et al.
6,254,550 B1 7/2001 McNamara et al.
6,348,068 B1 2/2002 Campbell et al.
6,419,695 B1 7/2002 Gabbay
6,419,696 B1 7/2002 Ortiz et al.
6,530,952 B2 3/2003 Vesely
6,533,783 B1 3/2003 Töllner
6,641,553 B1 11/2003 Chee et al.
6,752,813 B2 6/2004 Goldfarb et al.
6,790,229 B1 9/2004 Berreklouw
6,908,478 B2 6/2005 Alferness et al.
6,908,481 B2 6/2005 Cribier
6,964,684 B2 11/2005 Ortiz et al.
6,974,476 B2 12/2005 McGuckin, Jr. et al.
7,077,861 B2 7/2006 Spence
7,101,395 B2 9/2006 Tremulis et al.
7,125,421 B2 10/2006 Tremulis et al.
7,160,322 B2 1/2007 Gabbay
7,175,656 B2 2/2007 Khairkhahan
7,201,771 B2 4/2007 Lane
7,204,774 B2 4/2007 Dohogne
7,226,467 B2 6/2007 Lucatero et al.
7,329,279 B2 2/2008 Haug et al.
7,381,219 B2 6/2008 Salahieh et al.
7,400,000 B2 7/2008 Otsuka et al.
7,445,631 B2 11/2008 Salahieh et al.
7,445,634 B2 11/2008 Trieu
7,470,285 B2 12/2008 Nugent et al.
7,527,647 B2 5/2009 Spence
7,527,847 B2 5/2009 Roding
7,534,261 B2 5/2009 Freidman
7,563,267 B2 7/2009 Goldfarb et al.
7,594,903 B2 9/2009 Webler et al.
7,597,711 B2 10/2009 Drews et al.
7,604,646 B2 10/2009 Goldfarb et al.
7,608,091 B2 10/2009 Goldfarb et al.
7,618,449 B2 11/2009 Tremulis et al.
7,621,948 B2 11/2009 Herrmann et al.
7,666,204 B2 2/2010 Thornton et al.
7,704,269 B2 4/2010 St. Goar et al.
7,731,705 B2 6/2010 Wardle
7,748,389 B2 7/2010 Salahieh et al.
7,749,266 B2 7/2010 Forster et al.
7,780,725 B2 8/2010 Haug et al.
7,789,069 B2 9/2010 Rodriguez-Amaya et al.
7,799,069 B2 9/2010 Bailey et al.
7,804,048 B2 9/2010 Furman
7,811,296 B2 10/2010 Goldfarb et al.
7,824,442 B2 11/2010 Salahieh et al.
7,824,443 B2 11/2010 Salahieh et al.
7,841,298 B2 11/2010 Margerum et al.
7,846,203 B2 12/2010 Cribier
7,886,641 B2 2/2011 Wirth, Jr. et al.
7,942,927 B2 5/2011 Kaye et al.
7,947,075 B2 5/2011 Goetz et al.
7,951,195 B2 5/2011 Antonsson et al.
7,954,195 B2 6/2011 Hentosz
7,955,385 B2 * 6/2011 Crittenden ............ A61F 2/2466 623/2.11
7,959,666 B2 6/2011 Salahieh et al.
7,981,153 B2 7/2011 Fogarty et al.
7,986,724 B2 7/2011 Cooper et al.
7,988,724 B2 8/2011 Salahieh et al.
8,021,421 B2 9/2011 Fogarty et al.
8,034,102 B2 10/2011 Bullman-Fleming et al.
8,052,749 B2 11/2011 Salahieh et al.
8,052,750 B2 11/2011 Tuval et al.
8,062,355 B2 11/2011 Figulla et al.
8,070,800 B2 12/2011 Lock et al.
8,075,615 B2 12/2011 Eberhardt et al.
8,096,985 B2 1/2012 Legaspi et al.
8,147,541 B2 4/2012 Forster et al.
8,147,542 B2 4/2012 Maisano et al.
8,182,528 B2 5/2012 Salahieh et al.
8,216,256 B2 7/2012 Raschdorf et al.
8,236,049 B2 8/2012 Rowe et al.
8,241,351 B2 8/2012 Cabiri
8,251,977 B2 8/2012 Partlett
8,252,050 B2 8/2012 Maisano et al.
8,287,584 B2 10/2012 Salahieh et al.
8,313,526 B2 11/2012 Hoffman et al.
8,323,241 B2 12/2012 Salahieh et al.
8,323,336 B2 12/2012 Hill et al.
8,328,868 B2 12/2012 Paul et al.
8,343,213 B2 1/2013 Salahieh et al.
8,348,995 B2 1/2013 Tuval et al.
8,348,996 B2 1/2013 Tuval et al.
8,366,767 B2 2/2013 Zhang
8,398,708 B2 3/2013 Meiri et al.
8,403,981 B2 3/2013 Forster et al.
8,403,983 B2 3/2013 Quadri et al.
8,414,643 B2 4/2013 Tuval et al.
8,414,644 B2 4/2013 Quadri et al.
8,414,645 B2 4/2013 Dwork et al.
8,425,593 B2 4/2013 Braido et al.
8,449,599 B2 5/2013 Chau et al.
8,454,686 B2 6/2013 Alkhatib
8,465,504 B2 6/2013 Mohamed et al.
8,465,541 B2 6/2013 Dwork
8,500,800 B2 8/2013 Maisano et al.
8,512,401 B2 8/2013 Murray et al.
8,523,881 B2 9/2013 Cabiri et al.
8,545,553 B2 10/2013 Zipory et al.
8,556,963 B2 10/2013 Tremulis et al.
8,562,645 B2 10/2013 Stone et al.
8,562,673 B2 10/2013 Yeung et al.
8,579,962 B2 11/2013 Salahieh et al.
8,603,157 B2 12/2013 Seguin et al.
8,603,160 B2 12/2013 Salahieh et al.
8,623,075 B2 1/2014 Murray et al.
8,628,570 B2 1/2014 Seguin
8,641,727 B2 2/2014 Starksen et al.
8,652,202 B2 2/2014 Alon et al.
8,652,203 B2 2/2014 Quadri et al.
8,657,872 B2 * 2/2014 Seguin .................. A61F 2/2427 623/2.38
8,685,086 B2 4/2014 Navia et al.
8,696,693 B2 4/2014 Najafi et al.

(56) References Cited

U.S. PATENT DOCUMENTS 8,715,342 B2 5/2014 Zipory et al.
8,740,976 B2 6/2014 Tran et al.
8,744,031 B1 6/2014 Kim et al.
8,784,479 B2 7/2014 Antonsson et al.
8,790,367 B2 7/2014 Nguyen et al.
8,808,368 B2 8/2014 Maisano et al.
8,826,078 B2 9/2014 Chou et al.
8,828,078 B2 9/2014 Salahieh et al.
8,834,564 B2 9/2014 Tuval et al.
8,840,663 B2 9/2014 Salahieh et al.
8,840,664 B2 9/2014 Karapetian et al.
8,845,588 B2 9/2014 Bruszewski
8,852,271 B2 10/2014 Murray et al.
8,876,893 B2 11/2014 Dwork et al.
8,876,894 B2 11/2014 Tuval et al.
8,876,895 B2 11/2014 Tuval et al.
8,900,294 B2 12/2014 Paniagua et al.
8,911,494 B2 12/2014 Hammer et al.
8,920,369 B2 12/2014 Salahieh et al.
8,926,690 B2 1/2015 Kowalsky
8,926,696 B2 1/2015 Cabiri et al.
8,926,697 B2 1/2015 Gross et al.
8,940,002 B2 1/2015 Goertzen
8,940,044 B2 1/2015 Hammer et al.
8,951,299 B2 2/2015 Paul et al.
8,954,299 B2 2/2015 You et al.
8,986,371 B2 * 3/2015 Quill .................... A61F 2/2418 623/2.11
8,996,980 B2 3/2015 Chokshi
8,998,980 B2 4/2015 Shipley et al.
9,005,273 B2 4/2015 Salahieh et al.
9,011,515 B2 * 4/2015 Schweich, Jr. ....... A61F 2/2412 623/1.26
9,011,523 B2 4/2015 Seguin
9,011,530 B2 4/2015 Reich et al.
9,017,408 B2 4/2015 Siegal et al.
9,023,100 B2 5/2015 Quadri et al.
9,034,032 B2 5/2015 McLean et al.
9,039,757 B2 5/2015 McLean et al.
9,056,009 B2 6/2015 Keränen
9,061,120 B2 6/2015 Osypka et al.
9,078,747 B2 * 7/2015 Conklin ................ A61F 2/2418
9,095,431 B2 8/2015 Yu et al.
9,119,719 B2 9/2015 Zipory et al.
9,125,739 B2 9/2015 Paniagua et al.
9,125,740 B2 9/2015 Morriss et al.
9,132,009 B2 9/2015 Hacohen et al.
9,155,619 B2 10/2015 Liu et al.
9,168,129 B2 10/2015 Valdez et al.
9,168,131 B2 10/2015 Yohanan et al.
9,173,713 B2 11/2015 Hart et al.
9,173,737 B2 11/2015 Hill et al.
9,180,006 B2 11/2015 Keränen
9,226,823 B2 1/2016 Dwork
9,232,995 B2 1/2016 Kovalsky et al.
9,277,994 B2 3/2016 Miller et al.
9,289,297 B2 3/2016 Wilson et al.
9,295,547 B2 3/2016 Costello et al.
9,301,756 B2 4/2016 Wardle
9,301,836 B2 4/2016 Buchbinder et al.
9,307,980 B2 4/2016 Gilmore et al.
9,320,597 B2 4/2016 Savage et al.
9,343,224 B2 5/2016 Zilbershlag
9,358,110 B2 6/2016 Paul et al.
9,414,915 B2 8/2016 Lombardi et al.
9,427,315 B2 8/2016 Schweich et al.
9,439,757 B2 9/2016 Wallace et al.
9,468,134 B2 10/2016 Igarashi
9,468,525 B2 10/2016 Kovalsky
9,474,606 B2 10/2016 Zipory et al.
9,474,840 B2 10/2016 Siess
9,480,558 B2 11/2016 DeStefano
9,480,559 B2 11/2016 Vidlund et al.
9,492,273 B2 11/2016 Wallace et al.
9,526,487 B2 12/2016 Rahmani
9,526,609 B2 12/2016 Salahieh et al.
9,532,868 B2 1/2017 Braido
9,532,870 B2 1/2017 Cooper et al.
9,561,102 B2 2/2017 Rust et al.
9,579,198 B2 2/2017 Deem et al.
9,579,425 B2 2/2017 Gandhi
9,585,042 B2 2/2017 Parkvall et al.
9,636,224 B2 5/2017 Zipory et al.
9,636,481 B2 5/2017 Campbell et al.
9,662,202 B2 5/2017 Quill et al.
9,662,206 B2 5/2017 Börtlein et al.
9,662,209 B2 5/2017 Gross et al.
9,675,454 B2 6/2017 Vidlund et al.
9,681,952 B2 6/2017 Hacohen et al.
9,687,343 B2 6/2017 Börtlein et al.
9,724,192 B2 8/2017 Sheps et al.
9,730,790 B2 8/2017 Quadri et al.
9,730,793 B2 8/2017 Reich et al.
9,744,031 B2 8/2017 Girard et al.
9,744,038 B2 8/2017 Dahlgren et al.
9,750,605 B2 9/2017 Ganesan et al.
9,763,779 B2 9/2017 Börtlein et al.
9,763,780 B2 9/2017 Morriss et al.
9,814,611 B2 11/2017 Cartledge et al.
9,827,090 B2 11/2017 Hill et al.
9,861,480 B2 1/2018 Zakai et al.
9,867,700 B2 1/2018 Bakis et al.
9,867,702 B2 * 1/2018 Keränen ............... A61F 2/2451
9,877,833 B1 1/2018 Bishop et al.
9,882,341 B2 1/2018 Gapontsev et al.
9,883,941 B2 2/2018 Hastings et al.
9,889,003 B2 2/2018 Börtlein et al.
9,895,221 B2 2/2018 Vidlund
9,895,222 B2 2/2018 Zeng et al.
9,901,444 B2 2/2018 Valdez et al.
9,918,840 B2 3/2018 Reich et al.
D815,744 S 4/2018 Ratz et al.
9,949,825 B2 4/2018 Braido et al.
9,949,828 B2 4/2018 Sheps et al.
9,950,142 B2 4/2018 Eversull et al.
9,966,452 B2 5/2018 Oda
9,968,452 B2 5/2018 Sheps et al.
9,974,647 B2 5/2018 Ganesan et al.
9,974,650 B2 5/2018 Nguyen-Thien-Nhon et al.
9,999,502 B2 6/2018 Nasr et al.
9,999,504 B2 6/2018 Czyscon et al.
10,004,599 B2 6/2018 Rabito et al.
10,016,271 B2 7/2018 Morriss et al.
10,016,272 B2 * 7/2018 Spence ................ A61F 2/2418
10,016,274 B2 7/2018 Tabor et al.
10,028,832 B2 7/2018 Quill et al.
10,029,037 B2 7/2018 Muller et al.
10,034,747 B2 7/2018 Harewood
10,034,749 B2 7/2018 Spence et al.
10,039,637 B2 8/2018 Maimon et al.
10,045,846 B2 8/2018 Bonyuet et al.
10,052,198 B2 8/2018 Chau et al.
10,052,199 B2 8/2018 Spence et al.
10,058,318 B2 8/2018 Tegzes
10,058,321 B2 8/2018 Sampson et al.
10,058,424 B2 8/2018 Cooper et al.
10,064,718 B2 9/2018 Keidar
10,064,719 B2 9/2018 Börtlein et al.
10,070,954 B2 9/2018 Braido et al.
10,080,651 B2 9/2018 Börtlein et al.
10,092,400 B2 10/2018 Jimenez et al.
10,098,734 B2 10/2018 Hoang
10,105,217 B2 10/2018 Keränen
10,105,224 B2 10/2018 Buchbinder et al.
10,117,744 B2 11/2018 Ratz et al.
10,130,464 B2 11/2018 Meiri et al.
10,130,471 B2 11/2018 Keränen et al.
10,143,552 B2 12/2018 Wallace et al.
10,149,759 B2 12/2018 Naor
10,172,708 B2 1/2019 Anderson
10,172,711 B2 1/2019 Keränen
10,179,042 B2 1/2019 Braido et al.
10,188,514 B2 1/2019 Nasr
10,195,021 B2 2/2019 Keränen et al.

(56) References Cited

U.S. PATENT DOCUMENTS 10,195,025 B2 2/2019 Levi et al.
10,195,027 B2 2/2019 Nasr
10,195,028 B2* 2/2019 Hosmer ................ A61F 2/2418
10,195,029 B2* 2/2019 Keränen ............... A61F 2/2445
10,201,418 B2 2/2019 Biadillah et al.
10,206,775 B2 2/2019 Kovalsky et al.
10,213,307 B2 2/2019 Dwork et al.
10,226,330 B2 3/2019 Spence et al.
10,226,334 B2 3/2019 Rowe et al.
10,226,339 B2 3/2019 Spence et al.
10,238,489 B2 3/2019 Conklin
10,251,749 B2 4/2019 Zerkowski et al.
10,258,464 B2 4/2019 Delaloye et al.
10,258,468 B2 4/2019 Deem et al.
10,258,486 B2 4/2019 Ma et al.
10,265,169 B2 4/2019 Desrosiers et al.
10,271,950 B2 4/2019 Neustadter
10,299,917 B2 5/2019 Morriss et al.
10,299,921 B2 5/2019 Dale et al.
10,314,701 B2 6/2019 Von Segesser et al.
10,321,933 B1 6/2019 Ramee et al.
10,321,988 B2 6/2019 Gorman et al.
10,321,989 B2 6/2019 Keränen
10,327,743 B2 6/2019 St. Goar et al.
10,327,766 B2 6/2019 Zerkowski et al.
10,335,277 B2 7/2019 Crisostomo et al.
10,338,724 B2 7/2019 Zhao
10,350,066 B2 7/2019 Cooper et al.
10,357,351 B2 7/2019 Cooper et al.
10,357,354 B2 7/2019 Marton
10,357,634 B2 7/2019 Simmons et al.
10,363,130 B2 7/2019 Armer et al.
10,363,131 B2 7/2019 Eidenschink et al.
10,368,986 B2 8/2019 Gosal et al.
10,368,990 B2 8/2019 Noe et al.
10,376,266 B2 8/2019 Herman et al.
10,376,360 B2 8/2019 Bruchman et al.
10,376,363 B2 8/2019 Quadri et al.
10,398,547 B2 9/2019 Li et al.
10,426,608 B2 10/2019 Salahieh et al.
10,433,961 B2 10/2019 McLean
10,433,964 B2 10/2019 Wainscott
10,470,881 B2 11/2019 Noe et al.
10,478,291 B2 11/2019 Nguyen et al.
10,500,048 B2 12/2019 Khairkhahan et al.
10,507,104 B2 12/2019 Zhang et al.
10,512,541 B2 12/2019 Zerkowski et al.
10,524,901 B2 1/2020 Quadri et al.
10,524,904 B2 1/2020 O'Connell et al.
10,548,729 B2 2/2020 Zipory et al.
10,568,737 B2 2/2020 Noe et al.
10,575,951 B2 3/2020 Johnson et al.
10,603,165 B2 3/2020 Maimon et al.
10,639,143 B2 5/2020 Oba
10,639,154 B2 5/2020 Seguin
10,653,524 B2 5/2020 Khairkhahan et al.
10,660,753 B2 5/2020 Pham et al.
10,687,938 B2 6/2020 Patel et al.
10,695,160 B2 6/2020 Lashinski et al.
10,702,386 B2 7/2020 Khairkhahan et al.
10,709,552 B2 7/2020 Backus et al.
10,716,662 B2 7/2020 Delaloye et al.
10,722,351 B2 7/2020 Griffin et al.
10,722,352 B2 7/2020 Spence
10,722,353 B2 7/2020 Levi
10,722,359 B2* 7/2020 Patel ..................... A61F 2/2412
10,729,542 B2 8/2020 Howard et al.
10,743,991 B2 8/2020 Brown
10,751,180 B2 8/2020 Schewel
10,751,184 B2 8/2020 Reich et al.
10,765,514 B2 9/2020 Iflah et al.
10,813,749 B2 10/2020 Nguyen et al.
10,828,153 B2 11/2020 Noe et al.
10,856,970 B2 12/2020 Tuval et al.
10,869,755 B2 12/2020 Granada et al.
10,888,420 B2 1/2021 Bateman et al.
10,888,421 B2 1/2021 Hariton et al.
10,912,644 B2* 2/2021 Argento ................ A61F 2/2427
10,925,595 B2* 2/2021 Hacohen ............ A61B 17/0401
10,973,629 B2 4/2021 Levi et al.
10,973,630 B2 4/2021 Torrianni et al.
11,007,057 B2 5/2021 Pham et al.
11,020,221 B2 6/2021 Arcaro et al.
11,039,922 B2 6/2021 Konno
11,147,670 B2* 10/2021 Hayoz ................... A61F 2/2466
11,234,818 B2* 2/2022 Zerkowski ............ A61F 2/2409
11,471,282 B2 10/2022 Argento et al.
11,547,563 B2* 1/2023 Keränen ............... A61F 2/2466
11,672,657 B2* 6/2023 Argento ................ A61F 2/2418 623/2.11
11,833,034 B2* 12/2023 Argento ................ A61F 2/2418
11,986,389 B2* 5/2024 Argento ................ A61F 2/2427
11,992,334 B2* 5/2024 Belson ................. A61B 5/0002
12,102,526 B2 10/2024 Tamir
12,201,521 B2* 1/2025 Salahieh ............... A61F 2/2418
12,290,456 B2* 5/2025 Argento .................... A61F 2/88
2002/0151970 A1 10/2002 Garrison et al.
2002/0173841 A1 11/2002 Ortiz et al.
2002/0188344 A1 12/2002 Bolea et al.
2003/0114813 A1 6/2003 Dodge et al.
2003/0114913 A1 6/2003 Spenser et al.
2003/0233142 A1 12/2003 Morales et al.
2004/0030442 A1 2/2004 Speckhart et al.
2004/0039442 A1 2/2004 St. Goar et al.
2004/0044350 A1 3/2004 Martin et al.
2004/0133274 A1 7/2004 Webler et al.
2005/0038506 A1 2/2005 Webler et al.
2005/0137686 A1 6/2005 Salahieh et al.
2005/0137687 A1 6/2005 Salahieh et al.
2005/0137691 A1 6/2005 Salahieh et al.
2005/0137694 A1 6/2005 Haug et al.
2005/0137696 A1 6/2005 Salahieh et al.
2005/0165344 A1 7/2005 Dobak, III
2005/0240202 A1 10/2005 Shennib et al.
2005/0277839 A1 12/2005 Alderman et al.
2006/0000841 A1 1/2006 Smay et al.
2006/0009841 A1 1/2006 McGuckin, Jr. et al.
2006/0025858 A1 2/2006 Alameddine
2006/0052821 A1 3/2006 Abbot et al.
2006/0074484 A1 4/2006 Huber
2006/0178700 A1 8/2006 Quinn
2006/0184240 A1 8/2006 Jimenez et al.
2006/0195134 A1 8/2006 Crittenden
2006/0217762 A1 9/2006 Maahs et al.
2006/0241748 A1 10/2006 Lee et al.
2006/0259136 A1 11/2006 Nguyen et al.
2006/0293698 A1 12/2006 Douk
2007/0027533 A1 2/2007 Douk
2007/0038292 A1 2/2007 Danielpour
2007/0051377 A1 3/2007 Douk et al.
2007/0055206 A1 3/2007 To et al.
2007/0078302 A1 4/2007 Ortiz et al.
2007/0118151 A1 5/2007 Davidson
2007/0142907 A1 6/2007 Moaddeb et al.
2007/0185572 A1 8/2007 Solem et al.
2007/0255396 A1 11/2007 Douk et al.
2007/0293043 A1 12/2007 Singh et al.
2007/0293724 A1 12/2007 Saadat et al.
2007/0293943 A1 12/2007 Quinn
2008/0004696 A1 1/2008 Vesely
2008/0004697 A1 1/2008 Lichtenstein et al.
2008/0200980 A1* 8/2008 Robin .................. A61F 2/2418 623/2.11
2008/0208327 A1 8/2008 Rowe
2008/0275503 A1 11/2008 Spence et al.
2008/0275540 A1 11/2008 Wen
2009/0030504 A1 1/2009 Weber et al.
2009/0088836 A1 4/2009 Bishop et al.
2009/0093826 A1 4/2009 Warder-Gabaldon
2009/0138079 A1 5/2009 Tuval et al.
2009/0157174 A1 6/2009 Yoganathan et al.
2009/0192601 A1 7/2009 Rafiee et al.
2009/0209950 A1 8/2009 Starksen
2009/0222026 A1 9/2009 Rothstein et al.

(56) References Cited

U.S. PATENT DOCUMENTS

2009/0276040 A1 11/2009 Rowe et al.
2009/0299471 A1 12/2009 Keranen
2010/0010520 A1* 1/2010 Takahashi ............ A61B 17/064 606/157
2010/0030014 A1 2/2010 Ferrazzi
2010/0049239 A1 2/2010 McGuckin, Jr. et al.
2010/0076497 A1 3/2010 Zwirkoski
2010/0076549 A1 3/2010 Keidar et al.
2010/0094406 A1 4/2010 Leprince et al.
2010/0185172 A1 7/2010 Fabro
2010/0198056 A1 8/2010 Fabro et al.
2010/0198192 A1 8/2010 Serina et al.
2010/0198208 A1 8/2010 Napp et al.
2010/0217385 A1 8/2010 Thompson et al.
2010/0312333 A1 12/2010 Navia et al.
2011/0022164 A1 1/2011 Quinn et al.
2011/0040366 A1 2/2011 Goetz et al.
2011/0046600 A1 2/2011 Crank
2011/0082539 A1 4/2011 Suri
2011/0208298 A1 8/2011 Tuvai
2011/0224785 A1 9/2011 Hacohen
2011/0245911 A1 10/2011 Quill et al.
2011/0288637 A1 11/2011 De Marchena
2011/0313515 A1 12/2011 Quadri et al.
2011/0319989 A1 12/2011 Lane et al.
2012/0022633 A1 1/2012 Olson et al.
2012/0053680 A1 3/2012 Bolling et al.
2012/0053682 A1 3/2012 Kovalsky et al.
2012/0101572 A1 4/2012 Kovalsky et al.
2012/0123531 A1 5/2012 Tsukashima et al.
2012/0143316 A1 6/2012 Seguin et al.
2012/0165930 A1 6/2012 Gifford, III et al.
2012/0197388 A1 8/2012 Khairkhahan et al.
2012/0203333 A1 8/2012 McGuckin, Jr. et al.
2012/0221101 A1 8/2012 Moaddeb et al.
2012/0277734 A1 11/2012 Geotz et al.
2012/0277853 A1 11/2012 Rothstein
2013/0006352 A1 1/2013 Yaron
2013/0023985 A1 1/2013 Khairkhahan et al.
2013/0035758 A1 2/2013 Seguin et al.
2013/0079873 A1 3/2013 Migliazza et al.
2013/0109987 A1 5/2013 Kunis et al.
2013/0116779 A1 5/2013 Weber
2013/0123912 A1 5/2013 Tung et al.
2013/0172992 A1 7/2013 Gross et al.
2013/0253643 A1 9/2013 Rolando et al.
2013/0274873 A1 10/2013 Delaloye et al.
2013/0282113 A1 10/2013 Punga et al.
2013/0325110 A1 12/2013 Khalil et al.
2013/0331931 A1 12/2013 Gregg et al.
2014/0005768 A1 1/2014 Thomas et al.
2014/0031928 A1 1/2014 Murphy et al.
2014/0031930 A1 1/2014 Keidar et al.
2014/0081154 A1 3/2014 Toth
2014/0088696 A1 3/2014 Figulla et al.
2014/0194975 A1* 7/2014 Quill .................... A61F 2/2418 623/2.11
2014/0194983 A1 7/2014 Kovalsky et al.
2014/0200649 A1 7/2014 Essinger et al.
2014/0222136 A1 8/2014 Geist et al.
2014/0228943 A1 8/2014 Stigall et al.
2014/0249621 A1 9/2014 Eidenschink
2014/0257467 A1 9/2014 Lane et al.
2014/0257487 A1 9/2014 Lawson et al.
2014/0277382 A1 9/2014 Dolan et al.
2014/0277409 A1* 9/2014 Bortlein ................ A61F 2/2418 623/2.11
2014/0277427 A1 9/2014 Ratz et al.
2014/0296966 A1 10/2014 Braido et al.
2014/0324163 A1* 10/2014 Keranen ............... A61F 2/2448 29/419.1
2014/0350669 A1 11/2014 Gillespie et al.
2015/0005764 A1 1/2015 Hanson et al.
2015/0005874 A1 1/2015 Vidlund et al.
2015/0018876 A1 1/2015 Ewers et al.
2015/0051709 A1 2/2015 Vasquez et al.
2015/0094802 A1 4/2015 Buchbinder et al.
2015/0134055 A1 5/2015 Spence et al.
2015/0173897 A1 6/2015 Raanani et al.
2015/0230921 A1* 8/2015 Chau ....................... A61F 2/243 623/2.11
2015/0250480 A1 9/2015 Featherstone
2015/0265403 A1 9/2015 Keränen
2015/0272737 A1 10/2015 Dale et al.
2015/0297346 A1 10/2015 Duffy et al.
2015/0305863 A1 10/2015 Gray et al.
2015/0328000 A1 11/2015 Ratz et al.
2015/0335290 A1 11/2015 Hunter
2015/0335426 A1 11/2015 Lim et al.
2015/0351735 A1 12/2015 Keränen et al.
2015/0351908 A1 12/2015 Keränen et al.
2015/0351911 A1 12/2015 Keränen et al.
2016/0038087 A1 2/2016 Hunter
2016/0074165 A1* 3/2016 Spence ................. A61F 2/2418 623/2.37
2016/0089126 A1 3/2016 Guo
2016/0095705 A1 4/2016 Keränen et al.
2016/0113764 A1 4/2016 Sheahan et al.
2016/0143689 A1 5/2016 Ditter
2016/0143731 A1 5/2016 Backus et al.
2016/0151153 A1 6/2016 Sandstrom
2016/0166380 A1 6/2016 Seguin et al.
2016/0206853 A1 7/2016 Bolduc et al.
2016/0228247 A1 8/2016 Maimon et al.
2016/0235526 A1 8/2016 Lashinski et al.
2016/0235529 A1 8/2016 Ma et al.
2016/0310066 A1* 10/2016 Wiedenhoefer ...... G01C 22/006
2016/0310268 A1 10/2016 Oba
2016/0324637 A1 11/2016 Hlavka et al.
2016/0324639 A1 11/2016 Nguyen et al.
2016/0331523 A1 11/2016 Chau et al.
2016/0346080 A1 12/2016 Righini et al.
2017/0007402 A1* 1/2017 Zerkowski ............ A61F 2/2445
2017/0056163 A1 3/2017 Tayeb et al.
2017/0071732 A1 3/2017 Conklin et al.
2017/0078790 A1 3/2017 Yen et al.
2017/0079785 A1 3/2017 Li
2017/0079790 A1 3/2017 Vidlund et al.
2017/0112624 A1 4/2017 Patel
2017/0119524 A1 5/2017 Salahieh et al.
2017/0128203 A1 5/2017 Zhang et al.
2017/0156665 A1* 6/2017 Miller ................ A61B 5/14535
2017/0156723 A1 6/2017 Keating et al.
2017/0165054 A1 6/2017 Benson et al.
2017/0165057 A9 6/2017 Morriss et al.
2017/0189177 A1 7/2017 Schweich et al.
2017/0216025 A1 8/2017 Nitzan et al.
2017/0245850 A1 8/2017 Call et al.
2017/0258585 A1 9/2017 Marquez et al.
2017/0273788 A1 9/2017 O'Carroll et al.
2017/0273789 A1 9/2017 Yaron et al.
2017/0281341 A1 10/2017 Lim et al.
2017/0311937 A1 11/2017 Bambury et al.
2017/0348099 A1 12/2017 Mendelson et al.
2018/0008402 A1 1/2018 Braido et al.
2018/0021546 A1 1/2018 McDermott et al.
2018/0028177 A1 2/2018 van Oepen et al.
2018/0049868 A1 2/2018 Board et al.
2018/0049873 A1 2/2018 Manash et al.
2018/0055628 A1* 3/2018 Patel ..................... A61F 2/2418
2018/0092763 A1 4/2018 Dagan et al.
2018/0110622 A1 4/2018 Gregg et al.
2018/0116790 A1 5/2018 Ratz et al.
2018/0125649 A1 5/2018 Nasar
2018/0125651 A1 5/2018 Nasar et al.
2018/0133003 A1 5/2018 Levi
2018/0177592 A1 6/2018 Benichou et al.
2018/0177594 A1* 6/2018 Patel ..................... A61F 2/2418
2018/0206982 A1 7/2018 Haivatov et al.
2018/0206986 A1 7/2018 Noe et al.
2018/0206992 A1 7/2018 Brown
2018/0207395 A1 7/2018 Bulman et al.
2018/0214267 A1 8/2018 Lally et al.
2018/0214270 A1 8/2018 Subramanian et al.

(56) References Cited

U.S. PATENT DOCUMENTS

2018/0221014 A1 8/2018 Darabian
2018/0228608 A1 8/2018 Sheps et al.
2018/0228610 A1 8/2018 Lashinski et al.
2018/0235443 A1 8/2018 Smith et al.
2018/0250126 A1 9/2018 O'Connor et al.
2018/0250132 A1 9/2018 Ketal et al.
2018/0263764 A1* 9/2018 Manash ................ A61F 2/2427
2018/0280171 A1 10/2018 Gloss et al.
2018/0289473 A1 10/2018 Rajagopal et al.
2018/0289474 A1 10/2018 Rajagopal et al.
2018/0289478 A1 10/2018 Quill
2018/0289480 A1 10/2018 D'ambra et al.
2018/0289485 A1 10/2018 Rajagopal et al.
2018/0296335 A1 10/2018 Miyashiro
2018/0296338 A1 10/2018 Rabito et al.
2018/0318079 A1 11/2018 Patel et al.
2018/0325665 A1 11/2018 Gurovich et al.
2018/0333259 A1 11/2018 Dibie
2018/0344303 A1 12/2018 Bambury et al.
2018/0344454 A1 12/2018 Mauch et al.
2018/0344459 A1* 12/2018 Spence ................ A61F 2/2412
2018/0344971 A1 12/2018 Suzuki et al.
2018/0360599 A1 12/2018 Drasler et al.
2018/0360600 A1 12/2018 Zhuang et al.
2018/0368830 A1 12/2018 O'Carroll et al.
2019/0000615 A1 1/2019 Tayeb et al.
2019/0000625 A1 1/2019 O'Carroll et al.
2019/0008635 A1 1/2019 Francis et al.
2019/0008639 A1 1/2019 Landon et al.
2019/0008640 A1 1/2019 Cooper et al.
2019/0015205 A1 1/2019 Rajagopal et al.
2019/0021859 A1 1/2019 O'Carrol et al.
2019/0046315 A1 2/2019 Gao et al.
2019/0049239 A1 2/2019 Natroshvill et al.
2019/0053894 A1 2/2019 Levi et al.
2019/0053895 A1 2/2019 Levi
2019/0053898 A1 2/2019 Maimon et al.
2019/0053899 A1 2/2019 Levi
2019/0053903 A1 2/2019 Rohl et al.
2019/0060068 A1 2/2019 Cope et al.
2019/0060069 A1 2/2019 Maimon et al.
2019/0060071 A1 2/2019 Lane et al.
2019/0076244 A1 3/2019 Yohanan et al.
2019/0076664 A1 3/2019 Ollivier
2019/0117392 A1 4/2019 Quadri et al.
2019/0133756 A1 5/2019 Zhang et al.
2019/0133757 A1 5/2019 Zhang et al.
2019/0142589 A1 5/2019 Basude
2019/0159770 A1 5/2019 Rohl et al.
2019/0160292 A1 5/2019 Peichel et al.
2019/0167425 A1 6/2019 Reich et al.
2019/0175344 A1 6/2019 Khairkhahan
2019/0183649 A1 6/2019 Allen et al.
2019/0192288 A1 6/2019 Levi et al.
2019/0192296 A1 6/2019 Schwartz et al.
2019/0201191 A1 7/2019 McLean et al.
2019/0201200 A1* 7/2019 Conklin ................ A61F 2/2418
2019/0209311 A1 7/2019 Zhang et al.
2019/0209312 A1 7/2019 Zhang et al.
2019/0209313 A1 7/2019 Zhang et al.
2019/0209314 A1 7/2019 Zhang et al.
2019/0209315 A1 7/2019 Zhang et al.
2019/0209316 A1 7/2019 Zhang et al.
2019/0209317 A1 7/2019 Zhang et al.
2019/0209318 A1 7/2019 Zhang et al.
2019/0209320 A1 7/2019 Drasler et al.
2019/0231520 A1 8/2019 Desrosiers et al.
2019/0240023 A1 8/2019 Spence et al.
2019/0246916 A1 8/2019 Kuraguntla et al.
2019/0254816 A1 8/2019 Anderson et al.
2019/0261995 A1 8/2019 Goldfarb et al.
2019/0261996 A1 8/2019 Goldfarb et al.
2019/0261997 A1 8/2019 Goldfarb et al.
2019/0262129 A1 8/2019 Cooper et al.
2019/0282237 A1 9/2019 Goldfarb et al.
2019/0328515 A1 10/2019 Peterson et al.
2019/0328518 A1 10/2019 Neumann
2019/0336282 A1 11/2019 Christianson et al.
2019/0343625 A1 11/2019 Gharib et al.
2019/0365530 A1 12/2019 Hoang et al.
2019/0374337 A1 12/2019 Zamani et al.
2019/0374342 A1 12/2019 Gregg et al.
2020/0000579 A1 1/2020 Manash et al.
2020/0000586 A1 1/2020 Tian et al.
2020/0008936 A1 1/2020 Cheema et al.
2020/0022811 A1 1/2020 Griswold et al.
2020/0054453 A1 2/2020 Zerkowski et al.
2020/0060813 A1 2/2020 Nguyen et al.
2020/0060820 A1 2/2020 Ben-Zvi et al.
2020/0060852 A1* 2/2020 Argento .................... A61F 2/88
2020/0069415 A1 3/2020 Bialas et al.
2020/0078000 A1 3/2020 Rajagopal et al.
2020/0093601 A1 3/2020 Neustadter
2020/0107832 A1 4/2020 Eisinger et al.
2020/0107930 A1* 4/2020 Argento ................ A61F 2/2433
2020/0107932 A1* 4/2020 Rabito ............. A61B 17/06004
2020/0107933 A1* 4/2020 Oba ...................... A61F 2/2454
2020/0113586 A1 4/2020 Karasic et al.
2020/0113685 A1 4/2020 Miller et al.
2020/0113696 A1 4/2020 Ekvall et al.
2020/0138575 A1 5/2020 Tuval
2020/0139082 A1 5/2020 Matlock
2020/0178977 A1 6/2020 Coleman et al.
2020/0179109 A1 6/2020 Reimer et al.
2020/0188093 A1 6/2020 Wang et al.
2020/0188107 A1 6/2020 Gloss et al.
2020/0205800 A1 7/2020 Gilmore et al.
2020/0205969 A1 7/2020 Hacohen
2020/0205974 A1 7/2020 Zerkowski et al.
2020/0205975 A1 7/2020 Khairkhahan
2020/0205979 A1 7/2020 O'Carroll et al.
2020/0214708 A1* 7/2020 Sharma .............. A61B 17/1285
2020/0229806 A1 7/2020 Goldfarb et al.
2020/0229918 A1 7/2020 Pham et al.
2020/0229920 A1 7/2020 Wallace et al.
2020/0261220 A1* 8/2020 Argento ................ A61F 2/2418
2020/0269017 A1 8/2020 Winston et al.
2020/0275921 A1 9/2020 Gilmore et al.
2020/0276017 A1 9/2020 Subramanian et al.
2020/0297489 A1 9/2020 Bishop et al.
2020/0297491 A1* 9/2020 Argento ................ A61F 2/2457
2020/0306040 A1 10/2020 Fung et al.
2020/0323637 A1 10/2020 Banal et al.
2020/0352705 A1 11/2020 Heneghan et al.
2020/0352706 A1 11/2020 Campbell
2020/0360139 A1 11/2020 Hammer et al.
2021/0022854 A1 1/2021 Zhao et al.
2021/0022860 A1 1/2021 Lally et al.
2021/0030536 A1 2/2021 Kaleta
2021/0121289 A1 4/2021 Bruchman et al.
2021/0128297 A1 5/2021 Braido et al.
2021/0145573 A1 5/2021 Dasi et al.
2021/0154009 A1* 5/2021 Argento ................ A61F 2/2427
2021/0161688 A1 6/2021 Shahriari
2021/0177583 A1 6/2021 Colavito et al.
2021/0177584 A1 6/2021 Levi et al.
2021/0177587 A1 6/2021 Braido
2021/0186689 A1 6/2021 Eidenschink et al.
2021/0228343 A1 7/2021 Scheinblum et al.
2021/0315693 A1 10/2021 Tabor et al.
2021/0338419 A1 11/2021 Gifford, III et al.
2021/0378823 A1* 12/2021 Argento ................ A61F 2/2466
2021/0386542 A1 12/2021 Schankereli et al.
2021/0401572 A1 12/2021 Nasar et al.
2022/0054261 A1* 2/2022 Argento .................... A61F 2/95
2022/0134056 A1 5/2022 Roach et al.
2022/0175522 A1 6/2022 Salahleh et al.
2022/0226118 A1 7/2022 Keränen et al.
2022/0245911 A1 8/2022 Hu et al.
2022/0257373 A1* 8/2022 Yang ..................... A61F 2/2418
2022/0265311 A1 8/2022 Sorajja et al.
2022/0273430 A1 9/2022 Neustadter et al.
2022/0273434 A1 9/2022 Kheradvar et al.
2022/0387755 A1 12/2022 Higgins

(56) References Cited

U.S. PATENT DOCUMENTS

2022/0401214 A1* 12/2022 Saul ..................... A61F 2/2457
2023/0028648 A1 1/2023 Neuberger et al.
2023/0044256 A1 2/2023 Salahieh
2023/0048179 A1 2/2023 Zarbatany et al.
2023/0105492 A1 4/2023 Argento et al.
2023/0118748 A1 4/2023 Argento
2023/0165679 A1 6/2023 Boyd et al.
2023/0240839 A1 8/2023 Corona et al.
2023/0240849 A1* 8/2023 Backus ................ A61F 2/2409
623/2.11
2023/0380968 A1 11/2023 Orlov
2024/0008979 A1* 1/2024 Mulcahy .............. A61F 2/2457
2024/0024110 A1 1/2024 Marshall et al.
2024/0030536 A1 1/2024 Park et al.
2024/0041598 A1* 2/2024 Argento ............... A61F 2/2466
2024/0148497 A1 5/2024 Bukin et al.
2024/0177583 A1 5/2024 Adato et al.
2024/0285396 A1* 8/2024 Schwartz ............. A61F 2/2409
2024/0293217 A1 9/2024 Cartledge et al.
2024/0341951 A1* 10/2024 Argento ............... A61F 2/2418
2024/0374378 A1 11/2024 Adamek-Bowers et al.
2024/0415646 A1* 12/2024 Yang .................... A61F 2/2427
2025/0082472 A1* 3/2025 Brown ................. A61F 2/2457

FOREIGN PATENT DOCUMENTS

AU 2020227034 A1 9/2020
BR PI0820603 B1 6/2020
CA 2979817 A1 9/2016
CA 2954826 C 10/2019
CA 2920865 C 6/2023
CN 102869321 A 1/2013
CN 103764216 A 4/2014
CN 103974670 A 8/2014
CN 104968300 A 10/2015
CN 105358098 A 2/2016
CN 107690323 A 2/2018
CN 109843219 A 6/2019
CN 110314016 A 10/2019
CN 111110401 A 5/2020
CN 111110403 A 5/2020
CN 108601655 B 6/2020
CN 111265335 A 6/2020
CN 111278389 A 6/2020
CN 111329541 A 6/2020
CN 113288514 A 8/2021
DE 19857887 B4 5/2005
DE 102014102650 A1 9/2015
EP 1105181 B1 2/2004
EP 1867305 A2 12/2007
EP 1432369 B1 2/2008
EP 2374415 A1 10/2011
EP 2835112 A1 2/2015
EP 2907479 A1 8/2015
EP 3037064 A1 6/2016
EP 2556799 B1 10/2016
EP 3158975 A1 4/2017
EP 3342355 A1 7/2018
EP 3395296 A1 10/2018
EP 3406225 A1 11/2018
EP 3417831 A1 12/2018
EP 3476366 A1 5/2019
EP 3482718 A1 5/2019
EP 3102152 B1 8/2019
EP 2637607 B1 10/2019
EP 3554424 A1 10/2019
EP 3244809 B1 2/2020
EP 3639792 A1 4/2020
EP 3417831 B1 5/2020
EP 3649963 A2 5/2020
EP 2072027 B1 6/2020
EP 3441045 B1 7/2020
EP 3672528 A1 7/2020
EP 3554423 B1 8/2020
EP 3107498 B1 9/2020
EP 3570782 B1 9/2020
EP 3700467 A1 9/2020
EP 3705090 A1 9/2020
EP 3782585 A1 2/2021
EP 4548880 A2 5/2025
GB 2507053 A 4/2014
JP H08131551 A 5/1996
JP 2004154177 A 6/2004
JP 2008018139 A 1/2008
JP 2011506017 A 3/2011
JP 2012531270 A 12/2012
JP 2013525039 A 6/2013
JP 2014230797 A 12/2014
JP 2017506988 A 3/2017
JP 2017538540 A 12/2017
JP 2018515175 A 6/2018
JP 2019533531 A 11/2019
JP 2020515375 A 5/2020
JP 2020517379 A 6/2020
JP 2020520729 A 7/2020
JP 6735294 B2 8/2020
KR 2020032237 A 3/2020
KR 2020033349 A 3/2020
KR 2020033350 A 3/2020
TW 202027694 A 8/2020
WO WO00/69345 A1 11/2000
WO WO02/03892 A1 1/2002
WO WO-2006091163 A1 * 8/2006 .......... A61F 2/2448
WO WO2007/007873 A1 1/2007
WO WO2007/081820 A1 7/2007
WO WO2009/079475 A2 6/2009
WO WO2009/082479 A2 7/2009
WO WO2010/119445 A1 10/2010
WO WO2010/141847 A1 12/2010
WO WO2011/025945 A1 3/2011
WO WO2011/034973 A2 3/2011
WO WO2012/047644 A2 4/2012
WO WO2012/087842 A1 6/2012
WO WO2012/145545 A1 10/2012
WO WO2013/059747 A1 4/2013
WO WO2013/190910 A1 12/2013
WO WO2014/164151 A1 10/2014
WO WO2015/118464 A1 8/2015
WO WO2015/127264 A1 8/2015
WO WO2015/153755 A2 10/2015
WO WO2015/173609 A1 11/2015
WO WO2015/195823 A1 12/2015
WO WO2016/052145 A1 4/2016
WO WO2016/117169 A1 7/2016
WO WO2016/183485 A1 11/2016
WO WO2017/121193 A1 7/2017
WO WO2017/125170 A1 7/2017
WO WO2017/151566 A1 9/2017
WO WO2017/214098 A1 12/2017
WO WO2018/025260 A1 2/2018
WO WO2018/039561 A1 3/2018
WO WO2018/039589 A1 3/2018
WO WO2018/112429 A1 6/2018
WO WO2018/119304 A1 6/2018
WO WO-2018142186 A1 * 8/2018 .......... A61F 2/2448
WO WO2018/178966 A1 10/2018
WO WO2018/178967 A1 10/2018
WO WO2018/187390 A1 10/2018
WO WO2018/192197 A1 10/2018
WO WO2019/010370 A1 1/2019
WO WO2019/036592 A1 2/2019
WO WO2019/062366 A1 4/2019
WO WO2019/081777 A1 5/2019
WO WO2019/086958 A1 5/2019
WO WO2019/102484 A1 5/2019
WO WO2019/116369 A1 6/2019
WO WO2019/118371 A1 6/2019
WO WO2019/135011 A1 7/2019
WO WO2019/135028 A1 7/2019
WO WO2019/144036 A1 7/2019
WO WO2019/147504 A1 8/2019
WO WO2019/147846 A2 8/2019
WO WO2019/154124 A1 8/2019

(56) References Cited

FOREIGN PATENT DOCUMENTS

| | | | |
|---|---|---|---|
| WO | WO2019/164516 | A1 | 8/2019 |
| WO | WO2019/195860 | A2 | 10/2019 |
| WO | WO2019/209927 | A1 | 10/2019 |
| WO | WO2019/220384 | A1 | 11/2019 |
| WO | WO2019/222694 | A1 | 11/2019 |
| WO | WO2019/241777 | A1 | 12/2019 |
| WO | WO2019/246268 | A1 | 12/2019 |
| WO | WO2020/051147 | A1 | 3/2020 |
| WO | WO2020/051591 | A1 | 3/2020 |
| WO | WO2020/072199 | A1 | 4/2020 |
| WO | WO2020/072201 | A1 | 4/2020 |
| WO | WO2020/073050 | A1 | 4/2020 |
| WO | WO2020/106705 | A | 5/2020 |
| WO | WO2020/123719 | A1 | 6/2020 |
| WO | WO2020/157018 | A1 | 8/2020 |
| WO | WO2020/163112 | A1 | 8/2020 |
| WO | WO2020/180485 | A1 | 9/2020 |
| WO | WO2020/236830 | A1 | 11/2020 |
| WO | WO2020/247907 | A1 | 12/2020 |
| WO | WO2021/021482 | A1 | 2/2021 |
| WO | WO2021/028867 | A1 | 2/2021 |
| WO | WO2021/034497 | A1 | 2/2021 |
| WO | WO2021/035032 | A1 | 2/2021 |
| WO | WO2021/086850 | A1 | 5/2021 |
| WO | WO2021/091754 | A1 | 5/2021 |
| WO | WO2021/113143 | A1 | 6/2021 |
| WO | WO2021/178560 | A1 | 9/2021 |
| WO | WO2021/183610 | A1 | 9/2021 |
| WO | WO2021/257278 | A1 | 12/2021 |
| WO | WO2021/257722 | A1 | 12/2021 |
| WO | WO2022/010974 | A1 | 1/2022 |
| WO | WO2022/046678 | A1 | 3/2022 |
| WO | WO2022/047095 | A1 | 3/2022 |
| WO | WO2022/047160 | A1 | 3/2022 |
| WO | WO2022/047274 | A1 | 3/2022 |
| WO | WO2022/047393 | A8 | 3/2022 |
| WO | WO2022/047395 | A1 | 3/2022 |
| WO | WO2022/066713 | A1 | 3/2022 |
| WO | WO2022/066720 | A1 | 3/2022 |
| WO | WO2022/121057 | A1 | 6/2022 |
| WO | WO2022/174160 | A1 | 8/2022 |
| WO | WO202/271851 | A1 | 12/2022 |
| WO | WO2023/034936 | A1 | 3/2023 |
| WO | WO2023/049625 | A1 | 3/2023 |
| WO | WO2022/204138 | A1 | 9/2024 |

OTHER PUBLICATIONS

Westaby et al.; Adult human valve dimensions and their surgical significance; The American Journal of Cardiology; 53(4); pp. 552-556; Feb. 1984.
Argento et al.; U.S. Appl. No. 17/931,408 entitled "Prosthetic cardiac valve devices, systems, and methods," filed Sep. 12, 2022.
Argento et al.; U.S. Appl. No. 18/002,219 entitled "Minimal frame prosthetic cardiac valve delivery devices, systems, and methods," filed Dec. 16, 2022.
Adamek-Bowers et al.; U.S. Appl. No. 18/043,458 entitled "Prosthetic valve delivery system," filed Feb. 28, 2023.
Backus et al.; U.S. Appl. No. 18/004,609 entitled "Valve delivery system," filed Jan. 6, 2023.
Mulcahy et al.; U.S. Appl. No. 18/043,480 entitled "Prosthetic cardiac valve delivery devices, systems, and methods," filed Feb. 28, 2023.
Adamek-Bowers et al.; U.S. Appl. No. 18/043,499 entitled "Interface for prosthetic cardiac valve and delivery systems," filed Feb. 28, 2023.
Salahieh et al.; U.S. Appl. No. 18/043,519 entitled "Flared prosthetic cardiac valve delivery devices and systems," filed Feb. 28, 2023.
Scott et al.; U.S. Appl. No. 18/043,526 entitled "Access sheath for prosthetic cardiac valve delivery systems," filed Feb. 28, 2023.
Yang et al.; U.S. Appl. No. 18/043,542 entitled "Anchor for prosthetic cardiac valve devices," filed Feb. 28, 2023.
Argento et al.; U.S. Appl. No. 18/246,307 entitled "Systems, methods, and devices for expandable sensors," filed Mar. 22, 2023.
Argento et al.; U.S. Appl. No. 18/494,520 entitled "Prosthetic cardiac valve devices, systems, and methods," filed Oct. 25, 2023.
Mulcahy et al.; U.S. Appl. No. 18/573,816 entitled "Prosthetic cardiac valve delivery devices, systems, and methods," filed Dec. 22, 2023.
Argento et al.; U.S. Appl. No. 18/185,330 entitled "Prosthetic cardiac valve devices, systems, and methods," filed Mar. 16, 2023.
Adamek-Bowers et al.; U.S. Appl. No. 18/255,763 entitled "Mitral valve implants," filed Jun. 2, 2023.
Oakden et al.; U.S. Appl. No. 19/123,741 entitled"Prosthetic heart valve delivery system and method," filed Apr. 23, 2025.
Salahieh et al.; U.S. Appl. No. 19/217,801; entitled "Flared prosthetic cardiac valve delivery devices and systems," filed May 23, 2025.
Salahieh; U.S. Appl. No. 18/979,182 entitled "Anchor position verification for prosthetic cardiac valve devices," filed Dec. 12, 2024.
Boyd et al.; U.S. Appl. No. 18/873,271 entitled "Prosthetic heart valve delivery system and method," filed Dec. 9, 2024.
Masterclass; Knit vs. Woven: Learn How to Identify the Two Fabric Types; Jun. 7, 2021; 13 pages; retrieved from the internet (https://www.masterclass.com/articles/knit-vs-woven-learn-how-to-identify-the-two-fabric-types) on Nov. 15, 2024.
Boyd et al.; U.S. Appl. No. 18/688,735 entitled "Guide catheter for prosthetic cardiac valve delivery systems," filed Mar. 1, 2024.
Adamek-Bowers et al.; U.S. Appl. No. 18/693,856 entitled "Tether delivery of cardiac valve," filed Mar. 20, 2024.
Yang et al.; U.S. Appl. No. 18/700,621 entitled "Cardiac valve prosthesis delivery system and methods of use," filed Apr. 11, 2024.
Argento et al.; U.S. Appl. No. 18/639,743 entitled "Prosthetic cardiac valve devices, systems and methods," filed Apr. 18, 2024.
Adamek-Bowers et al.; U.S. Appl. No. 19/162,907 entitled "Prosthetic cardiac valve device, systems, and methods" filed Sep. 5, 2025.
Argento et al.; U.S. Appl. No. 19/305,151 entitled "Prosthetic cardiac valve devices, systems, and methods," filed Aug. 20, 2025.

* cited by examiner

PROSTHETIC CARDIAC VALVE SENSOR DEVICES, SYSTEMS, AND METHODS WITH IMAGING

CROSS-REFERENCE TO RELATED APPLICATIONS

This application claims priority to U.S. Provisional Patent Application No. 63/081,843, filed on Sep. 22, 2020, titled "PROSTHETIC CARDIAC VALVE SENSOR DEVICES, SYSTEMS, AND METHODS WITH IMAGING," the entirety of which is incorporated by reference herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Blood flow between heart chambers is regulated by native valves—the mitral valve, the aortic valve, the pulmonary valve, and the tricuspid valve. Each of these valves is a passive one-way valve that opens and closes in response to differential pressures. Patients with valvular disease have abnormal anatomy and/or function of at least one valve. For example, a valve may suffer from insufficiency, also referred to as regurgitation, when the valve does not fully close, thereby allowing blood to flow retrograde. Valve stenosis can cause a valve to fail to open properly. Other diseases may also lead to dysfunction of the valves.

The mitral valve, for example, sits between the left atrium and the left ventricle and, when functioning properly, allows blood to flow from the left atrium to the left ventricle while preventing backflow or regurgitation in the reverse direction. Native valve leaflets of a diseased mitral valve, however, do not fully prolapse, causing the patient to experience regurgitation.

While medications may be used to treat diseased native valves, the defective valve often needs to be repaired or replaced at some point during the patient's lifetime. Existing prosthetic valves and surgical repair and/or replacement procedures may have increased risks, limited lifespans, and/or are highly invasive. Some less invasive transcatheter options are available, but most are not ideal. A major limitation of existing transcatheter mitral valve devices, for example, is that the mitral valve devices are too large in diameter to be delivered transseptally, requiring transapical access instead. Furthermore, existing mitral valve replacement devices are not optimized with respect to strength-weight ratio and often take up too much space within the valve chambers, resulting in obstruction of outflow from the ventricle into the aorta and/or thrombosis.

Fluoroscopy and traditional imaging modalities can be employed during treatment of diseased native valves. However, most traditional imaging modalities do not enable clear imaging of tissue and/or may not clearly show the imaging of the prosthetic valve with the tissue.

Thus, a new valve device that overcomes some or all of these deficiencies is desired.

SUMMARY

The present disclosure generally relates to treating a diseased native valve in a patient and more particularly relates to prosthetic heart valves.

In general, in one embodiment, a prosthetic cardiac valve device for treating a diseased native valve of a heart includes a frame structure having a compressed configuration and an expanded configuration, a spiral anchor configured to be positioned around the frame structure and to anchor the frame structure to the native valve, and an image capture device attached to or positioned within the spiral anchor. The image capture device is configured to confirm placement of the spiral anchor within the heart.

This and other embodiments can include one or more of the following features. The spiral anchor can be configured to be fully advanced in the expanded configuration from an atrium of the heart through the native valve and into a ventricle of the heart. The image capture device can include an ultrasound transducer. The image capture device can include a radiopaque element. The radiopaque element can be a metal tip. The image capture device can be a camera. The camera can be disposed within an inflatable membrane filled with an inflation fluid. The membrane can be porous. The membrane can be configured to diffuse saline therethrough. The image capture device can be coupled to an external surface of the spiral anchor. The image capture device can be positioned within a central lumen of the spiral anchor. The image capture device can be coupled to a distal free end of the spiral anchor. The image capture device can include a plurality of sensors disposed along a length of the spiral anchor. The plurality of sensors can include an impedance sensor. The plurality of sensors can include a pressure sensor. The plurality of sensors can include a radiopaque element. A distal free end of the spiral wire can be configured to extend radially outward from a circumference of the spiral wire when the spiral wire is positioned around the frame structure. The frame structure can be configured to expand within the native valve. The compressed configuration can be sized and dimensioned for percutaneous insertion, and the expanded configuration can be sized and dimensioned for implantation in the native valve. The frame structure can include a first and second opposite ends. The first end can be configured to extend above the native valve and the second end can be configured to extend below the native valve when the frame structure is anchored to the native valve. The frame structure can include an expanded outer periphery in the expanded configuration and a compressed outer periphery when subject to an external radial force in the compressed configuration. The compressed outer periphery can be smaller in diameter than the expanded outer periphery. The frame structure can be self-expanding. The device can further include a valve segment within the frame structure having a biocompatible one-way valve. At least a portion of the valve segment can be positioned within at least a portion of the frame structure. The valve segment can include at least one leaflet having an inner layer and an outer layer. The frame structure can be attached to the outer layer at one or more ends of the frame structure. The valve segment can include a plurality of leaflets.

In general, in one embodiment, a delivery device for delivering a cardiac valve to a diseased native valve of a heart includes an outer sheath, an inner sheath extendable from the outer sheath configured to house a spiral anchor in an elongate configuration and to enable translation of the spiral anchor therethrough, and an image capture device attached to or positioned within a portion of the delivery device configured to confirm placement of the spiral anchor within the heart. The spiral anchor is configured to transition from the elongate configuration within the inner sheath to a spiral expanded configuration around chordae of the diseased native valve.

This and other embodiments can include one or more of the following features. The delivery device can further include a delivery guidewire advanceable through a lumen of the inner sheath. The image capture device can be coupled to the delivery guidewire. Retraction of the delivery guidewire into the lumen of the inner shaft can actuate the anchor into the expanded configuration. The inner sheath can be configured to assume a spiral configuration when extended from the outer sheath. The outer sheath can be steerable. The inner sheath can be steerable. The device can further include a distal valve capsule configured to hold a valve frame therein for delivery within the spiral anchor. The valve frame can be detachably coupled to the delivery device in the compressed configuration during delivery. The frame structure can be maintained in the compressed configuration by radial constriction from the outer sheath. Advancement of the inner shaft out of the lumen of the outer sheath can actuate the frame structure into the expanded configuration. The image capture device can include an ultrasound transducer. The image capture device can include a radiopaque element. The radiopaque element can be a metal tip. The image capture device can be a camera. The camera can be disposed within an inflatable membrane filled with an inflation fluid. The membrane can be porous. The membrane ca be configured to diffuse saline therethrough.

In general, in one embodiment, a method for treating a diseased native valve in a patient includes advancing a distal end of a delivery device that is detachable coupled to an anchor to a first side of a native valve, deploying the anchor from a delivery configuration to a deployed configuration on the first side of the native valve, advancing the anchor in the deployed configuration from the first side of the native valve to a second side of the native valve such that the anchor is located only on the second side of the native valve, rotating the anchor in the deployed configuration around chordae of the native valve, confirming a position of the anchor with an imaging source, and releasing the anchor from the distal end of the delivery device.

This and other embodiments can include one or more of the following features. The native valve can include a mitral valve. The first side of the native valve can include a left atrium. The second side of the native valve can include a left ventricle. The method can further include steering of the distal end of the delivery device. The steering can be guided by visualization of the native valve by the imaging source. The imaging source can be an image capture device coupled to the delivery device or the anchor. The image capture device can include two or more sensors. The method can further include identifying a position of the anchor relative to the chordae tendineae using the two or more sensors. Identifying the position of the anchor relative to the chordae tendineae can include the sequential sensing of the chordae tendinea by a first sensor and a second sensor. The method can further include modeling the heart. Modeling the heart can include producing a real-time model of the heart. The delivery configuration can be an elongated configuration, and the deployed configuration can be a spiral configuration. Deploying the anchor can include extending an inner sheath of the delivery device from an outer sheath of the inner sheath and advancing the anchor from the inner sheath. The method can further include advancing a delivery guidewire through the native valve. The delivery guidewire can include the imaging source. Advancing the anchor can include pushing the anchor in the deployed configuration through the native valve. The method can further include expanding a frame structure within the native valve from a compressed configuration to an expanded configuration after the step of rotating the anchor. The frame structure can include a first and second opposite ends. Expanding the frame structure can include expanding the frame structure such that the first end extends above the first side of the native valve and the second end extends below the second side of the native valve. The frame structure can be self-expanding. Expanding the frame structure can include releasing the frame structure from radial constriction by a delivery device. The frame structure can include a valve segment therewithin having a biocompatible one-way valve.

An aspect of the present disclosure provides a system for treating a diseased native valve in a patient. The system comprises a frame structure having a compressed configuration and an expanded configuration and an anchor comprising a wire having a free end and an imaging source. The anchor is configured to be fully advanced from an atrial side of a native valve in a patient into a ventricle of the heart and anchor the frame structure to the native valve when the frame structure is in the expanded configuration adjacent the native valve.

In some embodiments, the imaging source can comprise an image capture device. The image capture device can comprise an ultrasound transducer. The imaging source can comprise a fluoroscopy imaging system and the free end of the anchor can comprise a radiopaque element. The radiopaque element can be a metal tip. The image capture device can be a camera. The camera can be disposed within an inflatable membrane filled with an inflation fluid. The membrane can be porous. The membrane can be configured to diffuse saline therethrough. The imaging source can be coupled to the anchor. The imaging source can be positioned adjacent to the free end of the anchor. The imaging source can be coupled to the free end of the anchor. The imaging source can comprise a plurality of sensors disposed along a length of the anchor. The plurality of sensors can comprise an impedance sensor. The plurality of sensors can comprise a pressure sensor. The plurality of sensors can comprise a radiopaque element.

In some embodiments, the system further comprises a delivery device. The delivery device may comprise an outer sheath, and an inner sheath extendable from the outer sheath, wherein the inner sheath has a lumen through which the anchor is advanceable. The delivery device can further comprise a delivery guidewire advanceable through the lumen of the inner sheath, wherein the imaging source is coupled to the delivery guidewire. The inner sheath can be configured to assume a spiral or helical configuration when extended from the outer sheath. The outer sheath can have a lumen and can be configured to maintain the inner sheath in an elongated configuration when positioned within the lumen. The outer sheath can be steerable. The inner sheath can be steerable.

In some embodiments, the system further comprises a delivery device wherein the delivery device comprises an outer sheath, an inner shaft disposed within a lumen of the outer sheath, and a guidewire disposed within a lumen of the inner shaft. A proximal end of the anchor may be detachably coupled to the inner shaft during delivery to the native valve. The outer sheath may be steerable. The anchor can comprise an elongated configuration and a deployed configuration, wherein a proximal end of the anchor is detachably coupled to the inner shaft in the elongated configuration during delivery to the native valve, and wherein the anchor is configured to be actuated from the elongated configuration to the deployed configuration adjacent the native valve. Retraction of the guidewire into the lumen of the inner shaft can actuate the anchor into the deployed configuration.

In some embodiments, the imaging source comprises an image capture device. In some embodiments, the image capture device comprises a camera. The camera may be disposed within an inflatable membrane filled with an inflation fluid such as saline. The membrane may be porous. The membrane may be configured to diffuse inflation fluid therethrough. In some embodiments, the image capture device comprises an ultrasound transducer. In some embodiments, the imaging source comprises a fluoroscopy imaging system and the free end of the anchor comprises a radiopaque element. The radiopaque element may be a metal tip. The imaging source can be coupled to the anchor. The imaging source could be positioned adjacent to a free end of the anchor. The imaging source can be couple to the free end of the anchor.

In some embodiments, the imaging source comprises a sensor or a plurality of sensors disposed along the length of the anchor. The sensor can comprise an impedance sensor to detect contact with chordae. The sensor can comprise a camera to detect contact with chordae. The sensor can comprise a pressure sensor to detect contact with chordae.

In some embodiments, the delivery device comprises an outer sheath and an inner sheath extendable from the outer sheath, the inner sheath having a lumen through which the anchor is advanceable. The delivery device can further comprise a delivery guidewire advanceable through the lumen of the inner sheath, wherein the imaging source is coupled to the delivery guidewire. The inner sheath can be configured to assume a spiral or helical configuration when extended from the outer sheath. The outer sheath can have a lumen and can be configured to maintain the inner sheath in an elongated configuration when positioned within the lumen. The outer sheath can be steerable. The inner sheath can be steerable.

In some embodiments, the anchor may comprise an elongated configuration and a deployed configuration. The anchor may be configured to be actuated from the elongated configuration to the deployed configuration adjacent the native valve. Retraction of the guidewire into the lumen of the inner shaft may actuate the anchor into the deployed configuration. Alternatively or in combination, the anchor may be maintained in the elongated configuration by radial constriction from the outer sheath and advancement of the inner shaft out of the lumen of the outer sheath may actuate the anchor into the deployed configuration.

In some embodiments, the proximal end of the anchor may be detachably coupled to the inner shaft of the delivery device by radial constriction from the outer sheath. Retraction of the outer sheath away from the proximal end of the anchor may detach the anchor from the delivery device. Alternatively or in combination, the proximal end of the anchor may be detachably coupled to the inner shaft of the delivery device by an attachment element. Alternatively or in combination, the proximal end of the anchor may be detachably coupled to the inner shaft of the delivery device by a weak adhesive.

In some embodiments, the frame structure may be detachably coupled to the delivery device in the compressed configuration during delivery to the native valve. Expansion of the frame structure to the expanded configuration may detach the frame structure from the delivery device.

In some embodiments, the free end may comprise an atraumatic tip. For example, the free end may comprise a ball tip.

In some embodiments, the free end may be configured for piercing tissue.

In some embodiments, the wire may comprise a helical wire. Optionally, the anchor may comprise a first portion comprising the helical wire and another portion. Alternatively or in combination, the anchor may comprise a plurality of helical wires. For example, the anchor may comprise at least two helical wires having the same or different diameters. Alternatively or in combination, the anchor may comprise at least two helical wires having the same or different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the helical wire may have a generally cylindrical shape. The free end of the helical wire may extend radially outward from the cylindrical shape.

In some embodiments, the frame structure may be configured for expanding within the native valve of the patient.

In some embodiments, the compressed configuration may be sized and dimensioned for percutaneous insertion and the expanded configuration may be sized and dimensioned for implantation in the native valve of the patient.

In some embodiments, the frame structure may comprise a first and second opposite ends, the first end extending above a native valve and the second end extending below the native valve when the frame structure is anchored to the native valve.

In some embodiments, the frame structure may sit below the native valve when the frame structure is anchored to the native valve.

In some embodiments, the frame structure may comprise an expandable stent.

In some embodiments, the expanded configuration may have a generally tubular expanded shape.

In some embodiments, the frame structure may comprise an expanded outer periphery in the expanded configuration and a compressed outer periphery when subject to an external radial force in the compressed configuration. The compressed outer periphery may be smaller in diameter than the expanded outer periphery.

In some embodiments, the frame structure may be balloon-expandable.

In some embodiments, the frame structure may be self-expanding.

In some embodiments, the frame structure may be maintained in the compressed configuration by radial constriction from the outer sheath of the delivery device. Advancement of the inner shaft out of the lumen of the outer sheath may actuate the frame structure into the expanded configuration.

In some embodiments, the system may further comprise a valve segment within the frame structure comprising a biocompatible one-way valve. At least a portion of the valve segment may be positioned within at least a portion of the frame structure. The valve segment may comprise at least one leaflet having an inner layer and an outer layer. The frame structure may be attached to the outer layer at one or more ends of the frame structure. The valve segment may comprise a plurality of leaflets.

In another aspect, a method for treating a diseased native valve in a patient is provided. The method comprises positioning a distal end of a delivery device adjacent a native valve, wherein the distal end of the delivery device is detachably coupled to an anchor and a frame structure, visualizing the native valve as the distal end of the delivery device is positioned adjacent the native valve, wherein the native valve is visualized with an imaging source coupled to one or more of the delivery device or anchor, advancing a distal end of a delivery device from a first side of a native valve to a second side of the native valve, wherein the distal end of the delivery device is detachably coupled to an anchor and a frame structure, visualizing the native valve as the distal end of the delivery device is advanced from the first side of the native valve to a second side of the native valve, fully deploying the anchor on the second side of the native valve, releasing the anchor from the distal end of the delivery device, expanding the frame structure within the native valve from a compressed configuration to an expanded configuration, releasing the frame structure from the distal end of the delivery device, and retracting the delivery device from the native valve. In some embodiments, the steering of the distal end of the delivery device is guided by visualization of the native valve by the imaging source. In some embodiments, the imaging source comprises two or more sensors. The method can further comprise identifying a position of the anchor relative to the chordae tendineae, wherein the two or more sensors can be configured to indicate a position of the anchor relative to the chordae tendineae. Encircling of the chordae tendineae can be identified by the sequential sensing of the chordae tendineae by a first sensor and a second sensor.

In some embodiments, the method may further comprise steering the distal end of the delivery device such that the distal end of the delivery device points towards the first side of the native valve. Steering of the distal end of the delivery device can be guided by visualization of the native valve by the imaging source. The imaging source can comprise two or more sensors. The method can further comprise identifying a position of the anchor relative to the chordae tendinea using the two or more sensors. Identifying the position of the anchor relative to the chordae tendinea can comprise the sequential sensing of the chordae tendineae by a first sensor and a second sensor. Visualizing can comprise modeling the heart. Modeling the heart can comprise a real-time model of the heart.

In some embodiments, the method comprises steering the distal end of the delivery device such that the distal end of the delivery device points towards the first side of the native valve.

In some embodiments, fully deploying the anchor may comprise actuating the anchor from an elongated configuration to a deployed configuration.

In some embodiments, fully deploying the anchor comprises extending an inner sheath of the delivery device from an outer sheath of the inner sheath and advancing the anchor from the inner sheath. The method may further comprise advancing a delivery guidewire through the native valve and advancing the inner sheath over the delivery guidewire through the native valve.

In some embodiments, fully deploying the anchor may comprise actuating the anchor from an elongated configuration to a deployed configuration on the first side of the native valve and advancing the anchor in the deployed configuration through the native valve to the second side of the native valve. Advancing the anchor may comprise pushing the anchor through the native valve. Advancing the anchor may further comprise rotating the anchor through the native valve.

In some embodiments, fully deploying the anchor may comprise positioning the anchor such that it is located only on the second side of the native valve.

In some embodiments, the frame structure may comprise a first and second opposite ends. Expanding the frame structure may comprise expanding the frame structure such that the first end extends above the first side of the native valve and the second end extends below the second side of the native valve.

In some embodiments, expanding the frame structure may comprise expanding at least a portion the frame structure within at least a portion of the deployed anchor to anchor the frame structure to the native valve.

In some embodiments, expanding the frame structure and releasing the frame structure may occur simultaneously.

In some embodiments, the frame structure may be balloon-expandable. Expanding the frame structure may comprise inflating a balloon disposed within the frame structure. Inflation of the balloon may cause expansion of the frame structure.

In some embodiments, the frame structure may be self-expanding. Expanding the frame structure may comprise releasing the frame structure from radial constriction by the delivery device.

In some embodiments, the anchor may comprise a wire having a free end. The method may further comprise rotating the free end of the deployed anchor around one or more structures on the second side of the native valve. The one or more structures may comprise one or more valve leaflets of the native valve. Alternatively or in combination, the one or more structures may comprise one or more chordae of the left ventricle.

In some embodiments, the free end of the wire may comprise an atraumatic tip. For example, the free end may comprise a ball tip.

In some embodiments, the free end of the wire may be configured for piercing tissue.

In some embodiments, the wire may comprise a helical wire. Optionally, the anchor may comprise a first portion comprising the helical wire and another portion. Alternatively or in combination, the anchor may comprise a plurality of helical wires. For example, the anchor may comprise at least two helical wires having the same or different diameters. Alternatively or in combination, the anchor may comprise at least two helical wires having the same or different winding pitches.

In some embodiments, the helical wire may have a generally tubular shape. The free end of the helical wire may extend radially outward from the tubular shape.

In some embodiments, the helical wire may have a generally frustoconical shape. The free end of the helical wire may extend radially outward from the frustoconical shape.

In some embodiments, the helical wire may have a generally cylindrical shape. The free end of the helical wire may extend radially outward from the cylindrical shape.

In some embodiments, the frame structure may further comprise a valve segment within the frame structure comprising a biocompatible one-way valve.

In some embodiments, the native valve may be in a heart of a patient. The method may further comprise transseptally inserting the distal end of the delivery device into a left atrium of the heart. Alternatively or in combination, the native valve may comprise a mitral valve, the first side of the native valve may comprise a left atrium, and the second side of the native valve may comprise a left ventricle.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to systems and devices useful in sensing biological parameters in a subject and methods of use thereof. However, one of skill in the art will appreciate that this is not intended to be limiting and the devices and methods disclosed herein may be used in other anatomical areas and in other surgical procedures.

Figure 5:
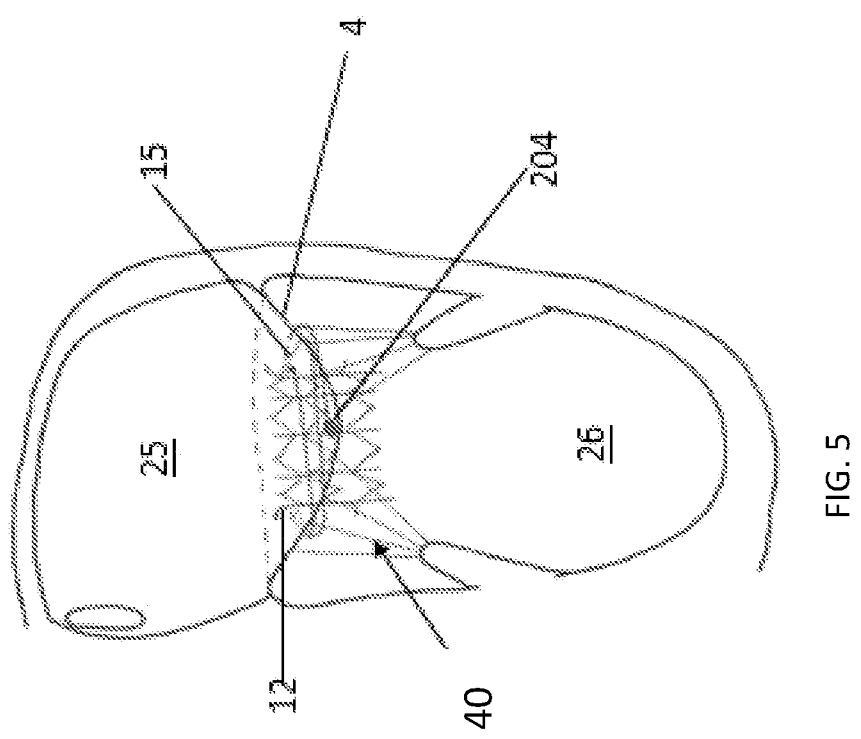
FIG. 5 shows a section view of a valve prothesis secured by an anchor at a diseased native valve, in accordance with some embodiments.

Described herein is a cardiac valve device for replacement of a valve, such as a mitral valve. As shown in FIG. 5, the cardiac valve device may include an expandable valve frame 12 surrounded by a spiral anchor 15. An imaging capture device 204 can be positioned on the anchor 15. Alternatively or additionally, as can be seen in FIGS. 2E-2G, in some embodiments, the image capture device 204 may be on the end of a delivery system 30, such as an anchor delivery guide wire 210.

The cardiac valve device described herein can be used to repair or replace a valve of the subject, such as a heart valve 4 (e.g., a mitral valve, a pulmonary valve, a tricuspid valve, or an aortic valve). The cardiac valve device can be introduced into a subject (e.g., via delivery device 30 as shown in FIGS. 2A-2X and 4A-4F). In some embodiments, the cardiac valve device disclosed herein can be delivered transseptally or transapically. In some embodiments, treating a subject (e.g., patient) can include positioning the cardiac valve device described herein the native valve 4.

In some embodiments, the distal end of the delivery device 20 may be configured to be advanced from a first side of a native valve 4 to a second side of the native valve 4. For example, the distal end of the delivery device 20 may be advanced from a left atrial side of a mitral valve to a left ventricular side of a mitral valve. In some embodiments, the distal end of the delivery device 30 may be transseptally inserted into the left atrium of the heart prior to advancement into the left ventricle. Alternatively, or in combination, the distal end of the delivery device 30 may be steerable such that it is positionable to point towards the first side of the native valve before being advanced to the second side of the native valve. A steerable delivery device 30 can be particularly useful in cases when the delivery device 30 is navigated through a tortuous path.

In some embodiments, fully deploying the anchor 15 of the cardiac valve device may include actuating the anchor 15 from an elongated delivery configuration to a deployed configuration on the first side of the native valve 4 and advancing the anchor 15 in the deployed configuration through the native valve 4 to the second side of the native valve. Advancing the anchor 15 may include pushing the anchor 15 through the native valve 4. Advancing the anchor 15 may further include rotating the anchor 15 through the native valve 4.

In some embodiments, fully deploying the anchor 15 may involve the use of an imaging source (e.g., to aid in positioning of the anchor 15). The use of an imaging source can, for example, advantageously enable visualization of deployment and/or anchoring (encircling of chordae). For example, the imaging source can be used to monitor and/or confirm the placement of the anchor 15 around the chordae tendineae.

Figure 1:
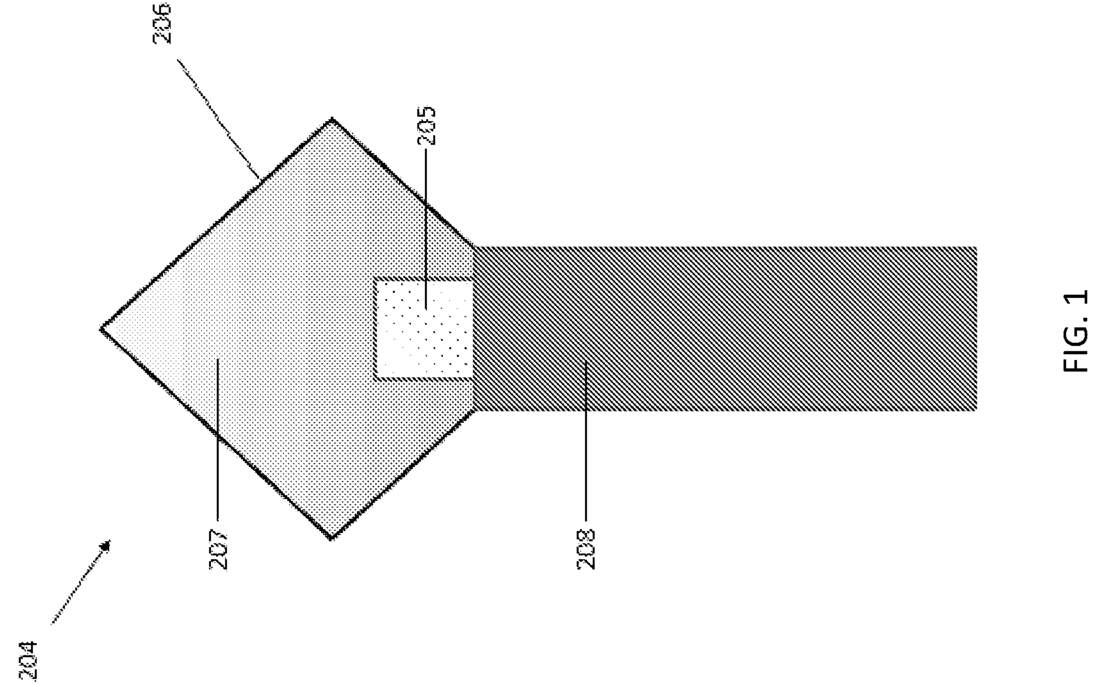
FIG. 1 shows a diagram of an image capture device.

In some embodiments, the imaging source can be an image capture device 204 (e.g., as shown in FIGS. 1 and 5). In some embodiments, the image capture device 204 may include a camera, such as an endoscopic camera. In some embodiments, the image capture device 204 can include a sensor. In some embodiments, the image capture device 204 can include a fiber optic. In some embodiments, the image capture device 204 can include an X-ray image intensifier or a flat-panel detector for fluoroscopy. In some embodiments, the image capture device 204 can be powered by a wire connected to an external device. In some embodiments, the image capture device 204 can be powered wirelessly, such as by inductive coupling.

In some embodiments, the image capture device 204 can be positioned on the anchor 15. For example, the imaging capture device can include a series of elements (e.g., sensors or cameras) disposed along the length of the anchor 15. In some embodiments, positioning the image capture device 204 at or proximate to the distal tip of the anchor 15 can enable the clinician to see if the anchor 15 abuts the atrial wall.

In some embodiments, the image capture device 204 may be located at or adjacent an anchor delivery guidewire, anchor delivery sheath, or other component of the delivery device 30. In some embodiments, the image capture device 204 may include an image capture element, such as a charge-coupled device (CCD), located at a handle or hub of the delivery device 30 and a fiber optic leading from the handle or hub to a location at or adjacent the anchor delivery guidewire, anchor delivery sheath, or other component of the delivery device 30.

The image capture device 204 may capture light-based images, such as images in the visible or infrared wavelengths. In some embodiments, the image capture device 204 may include an ultrasound transducer. In some embodiments, the image capture device 204 may be configured to perform 3D ultrasound imaging. Alternatively, or in combination, the imaging capture device 204 may include a radiographic imaging system (such as a fluoroscopy system) which may be used to guide and/or monitor deployment of the cardiac valve device. In some embodiments, the fluoroscopy system comprises an X-ray image intensifier.

In some embodiments, the image capture device 204 may include one or more optical fibers. An optical fiber, as described herein, may include an optical core to transmit an optical signal and an optical cladding to confine the optical signal within the core. The refractive indexes of the core may be greater than the refractive index of the cladding. The optical fiber may include graded-index (GRIN) fiber segments. The optical fiber may be shaped into a lens on a distal end of a fiberoptic cable.

In some embodiments, the optical fiber may be an LED (light-emitting diode) optical fiber to provide light to be captured by optical fibers bundled in a fiberoptic cable. An LED fiber as described herein may include an LED on a proximal end of an optical fiber. Light from the LED can be refracted through the LED fiber to a distal end of the LED fiber. In some embodiments, the LED fiber can be threaded through a lumen of the delivery system 30 (e.g., through a lumen of the inner sheath) to provide light for a fiberoptic cable to transmit an image from a camera on a distal end of the fiberoptic cable to a proximal end of the fiberoptic cable where it can be recorded by an imaging system. In some embodiments, the LED fiber can run through a lumen of the anchor 15 to another element of the image capture device 204, such as a camera on the distal end of the anchor 15. In some embodiments, the distal end of the anchor 15 may be abraded (e.g., with sandblasting) to create one or more apertures at the distal end of the anchor 15. The apertures may be on the tip of the distal end of the anchor 15 or the side of the distal end of the anchor. The LED fiber can run to the aperture such that the light from the LED fiber can illuminate the distal end of the anchor 15. In some embodiments, the LED fiber can include layers of masking or grating to capture a broad range of wavelengths. Different wavelengths of light captured by the LED fiber can be used to monitor pressure, force, acceleration, vibration, electromagnetic fields, etc.

In some embodiments, the image capture device 204 can include one or more sensors disposed along the length of the anchor 15 (e.g., a series of sensors disposed along the length of the anchor 15). The one or more sensors can include an impedance sensor to detect contact with chordae. The one or more sensors can include a capacitive sensor to measure the change in capacitance between two electrodes separated by a dielectric material. The capacitive sensor can be located along the length of the anchor 15 such that when the anchor 15 comes in contact with the chordae tendineae, the difference between the capacitance of blood within the heart and the tissue of the chordae tendineae will be measured. The change in measured capacitance may indicate that the particular sensor is in contact with the chordae tendineae. The one or more sensors can be configured to send a signal to a computer. The computer can then indicate that the chordae tendineae have been contacted by a sensor when a capacitance change occurs at the sensor.

The one or more sensors can include a photo-sensitive sensor to detect contact with chordae. The one or more sensors can include a camera. The one or more sensors can include a photoelectric sensor. The photoelectric sensor may include an infrared light transmitter and diffuse photo sensor. The photoelectric sensor may include a balloon filled with saline or another suitable fluid.

The one or more sensors can include a pressure sensor to detect contact with chordae tendineae. The pressor sensor can comprise one or more of a strain gauge, a force-sensitive resistor, or a microelectromechanical system. The pressor sensor can comprise a piezoelectric element. The pressure sensor can sense a change in pressure on the anchor. The one or more sensors can be configured to send a signal to a computer. The computer can then indicate that the chordae tendineae has been contacted by a sensor when a change in pressure occurs at the sensor.

Figure 7:
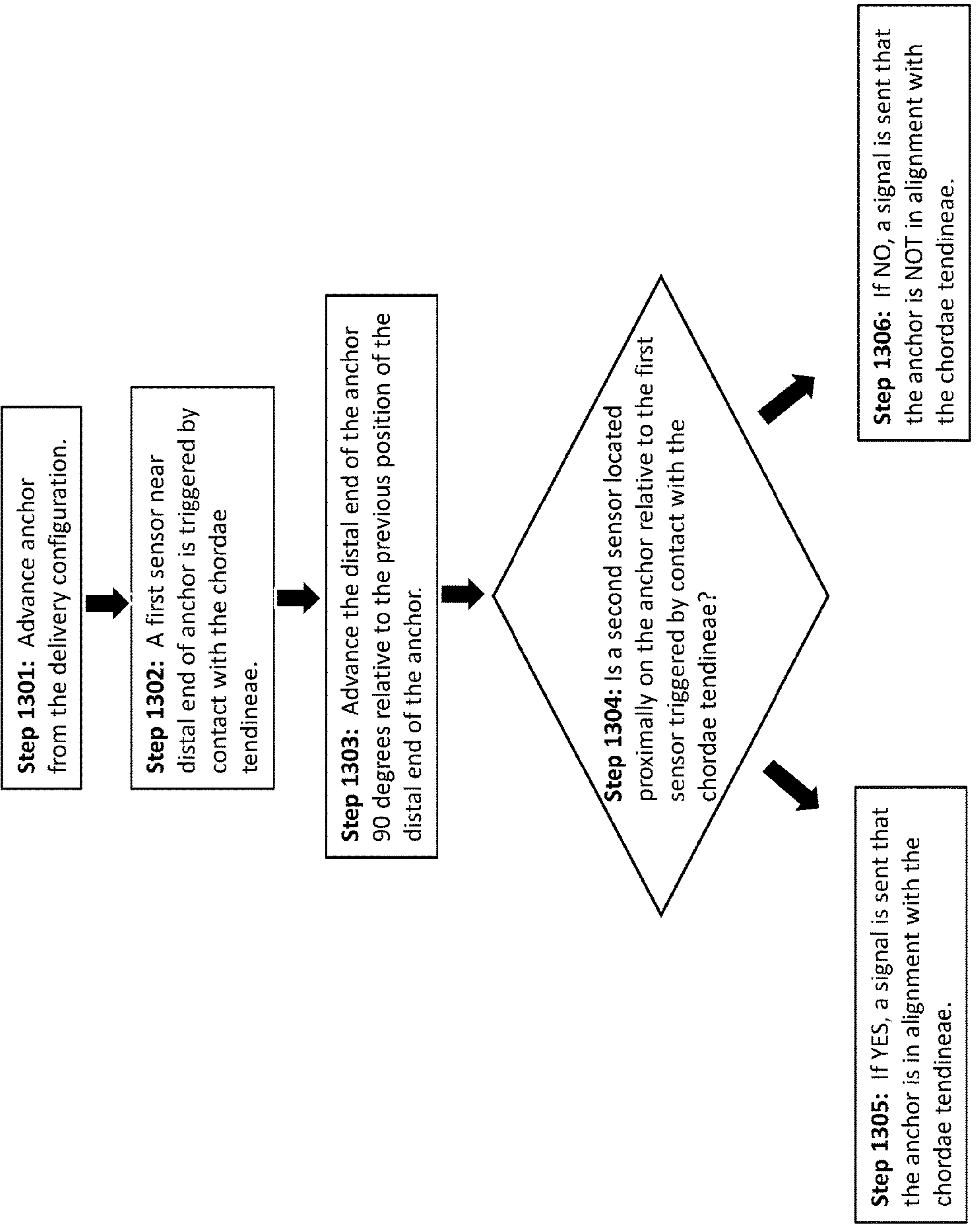
FIG. 7 shows a flowchart of a sensor monitored anchor delivery method.

In some embodiments, the image capture device 204 (e.g., one or more sensors) can be configured to send a signal to a user that encircling of the chordae tendineae by the anchor 15 is in progress if the chordae tendineae stimulate a first sensor and a second sensor in sequence. FIG. 7 shows an exemplary method of monitoring anchor delivery with an image capture device 204 including a plurality of sensors. At step 1301, the anchor 15 can be advanced from the delivery configuration. At step 1302, a first sensor near the distal end of the anchor 15 can be triggered by contact with the chordae tendineae. At step 1303, the distal end of the anchor 15 can be advanced 90 degrees relative to the previous position of the distal end of the anchor 15. At step 1304, it can be determined whether a second sensor located proximally on the anchor 15 relative to the first sensor is triggered by contact with the chordae tendineae. If the second sensor is triggered (step 1305), then a signal can be sent that the anchor 15 is in alignment with the chordae tendineae. If the second sensor is not triggered (step 1306), then a signal can be sent that the anchor 15 is not in alignment with the chordae tendineae. In other words, if the second sensor is not stimulated after a rotation of the anchor 15 (e.g., a 90 degree rotation of the distal end of the anchor 15 relative to the first position of the distal end of the anchor), a computer tracking the sensors will indicate that the anchor is not encircling the chordae tendinea. If the second sensor is not stimulated within an expected period of time after stimulation of the first sensor, such as a predetermined time to achieve 90 degrees of rotation of the anchor 15, a computer tracking the sensors will indicate that the anchor 15 is not encircling the chordae tendineae. Failure to encircle the chordae tendineae can be due to deformation of the anchor 15, entanglement of the anchor 15, etc. In response, the anchor 15 can be withdrawn and the process of encircling the chordae tendineae with the anchor 15 can begin again after re-alignment of the anchor relative to the chordae tendineae. The sensors can be disposed along the length of an anchor 15 such that a user can identify the position the anchor 15 relative to the chordae. The anchor 15 can comprise more than 20, 19, 18, 17, 16, 15, 14, 13, 12, 11, 10, 9, 8, 7, 6, 5, 4, 3, 2, or 1 sensor. The sensors can be regularly spaced along the length of the anchor 15. The sensors can be irregularly spaced along the length of the anchor 15. The sensors can be located on the side of the anchor 15 facing the chordae tendineae. The sensors can be located on the side of the anchor 15 not facing the chordae tendineae, for example, to identify contact with the walls of the chamber of the heart. The sensors can be located on the anchor 15 to indicate that the anchor 15 has been released from the delivery device. The length between sensors disposed along the anchor 15 can be greater than 10 cm, 9 cm, 8 cm, 7 cm, 6 cm, 5 cm, 4 cm, 3 cm, 2 cm, or 1 cm. The length between sensors along the anchor 15 can be less than 1 cm, 2 cm, 3 cm, 4 cm, 5 cm, 6 cm, 7 cm, 8 cm, 9 cm, or 10 cm. The length between sensors can be within a range bounded by any two of the following values: 1 cm, 2 cm, 3 cm, 4 cm, 5 cm, 6 cm, 7 cm, 8 cm, 9 cm, or 10 cm.

In some embodiments the image capture device 204 may be used to produce a real-time model of the heart. In some embodiments, the image capture device 204 may be used to produce a real-time model of the left ventricle. The real-time model of the heart may be produced using a computer system. The computer system may be directly connected to the image capture device 204. The computer system may be directly connected to the image capture device 204. The computer system may be remotely accessed by an intermediary device connected to the image capture device 204. Alternatively or in combination, the model of the heart may be produced by uploading individual images to a server to be combined later as an image of the heart or only the ventricle. The server may be a cloud server.

FIG. 1 shows a representative example of an image capture device 204 including an optical element 205 housed in a tubular element 208 (e.g., which can be the anchor 15), covered by a transparent membrane 206 filled with saline 207 or other suitable fluid. In some embodiments, the transparent membrane 206 may include an inflatable balloon. As can be seen in FIG. 1, in some embodiments, the image capture device 204 may be located within or extending from a lumen of the tubular element (e.g., the anchor 15 or a portion of the delivery device 30). In some embodiments, the image capture device 204 may be located adjacent to the tubular element (e.g., the anchor 15 or a portion of the delivery device 30).

In some embodiments, the optical element 205 may include a camera configured to detect wavelengths of light. Further, in some embodiments, the transparent membrane 206 may include a porous membrane through which saline can be diffused into the heart. Saline diffusion may increase transmission of light from an image capture device comprising a camera through the surrounding blood inside the heart to facilitate imaging of the structures of the heart. The membrane 206 may have a pore size greater than about 0.1 microns (μm), 0.2 μm, 0.3 μm, 0.4 μm, 0.5 μm, 0.6 μm, 0.7 μm, 0.8 μm, 0.9 μm, 1.0 μm, 1.1 μm, 1.2 μm, 1.3 μm, 1.4 μm, 1.5 μm, 1.6 μm, 1.7 μm, 1.8 μm, 1.9 μm, or 2.0 μm. The membrane 206 may have a pore size less than about 2.0 μm, 1.9 μm, 1.8 μm, 1.7 μm, 1.6 μm, 1.5 μm, 1.4 μm, 1.3 μm, 1.2 μm, 1.1 μm, 1.0 μm, 0.9 μm, 0.8 μm, 0.7 μm, 0.6 μm, 0.5 μm, 0.4 μm, 0.3 μm, 0.2 μm, or 0.1 μm. The membrane 206 may have a pore size within a range of about 0.1 μm to about 2.0 μm.

Figures 2A, 2B, 2C, 2D:
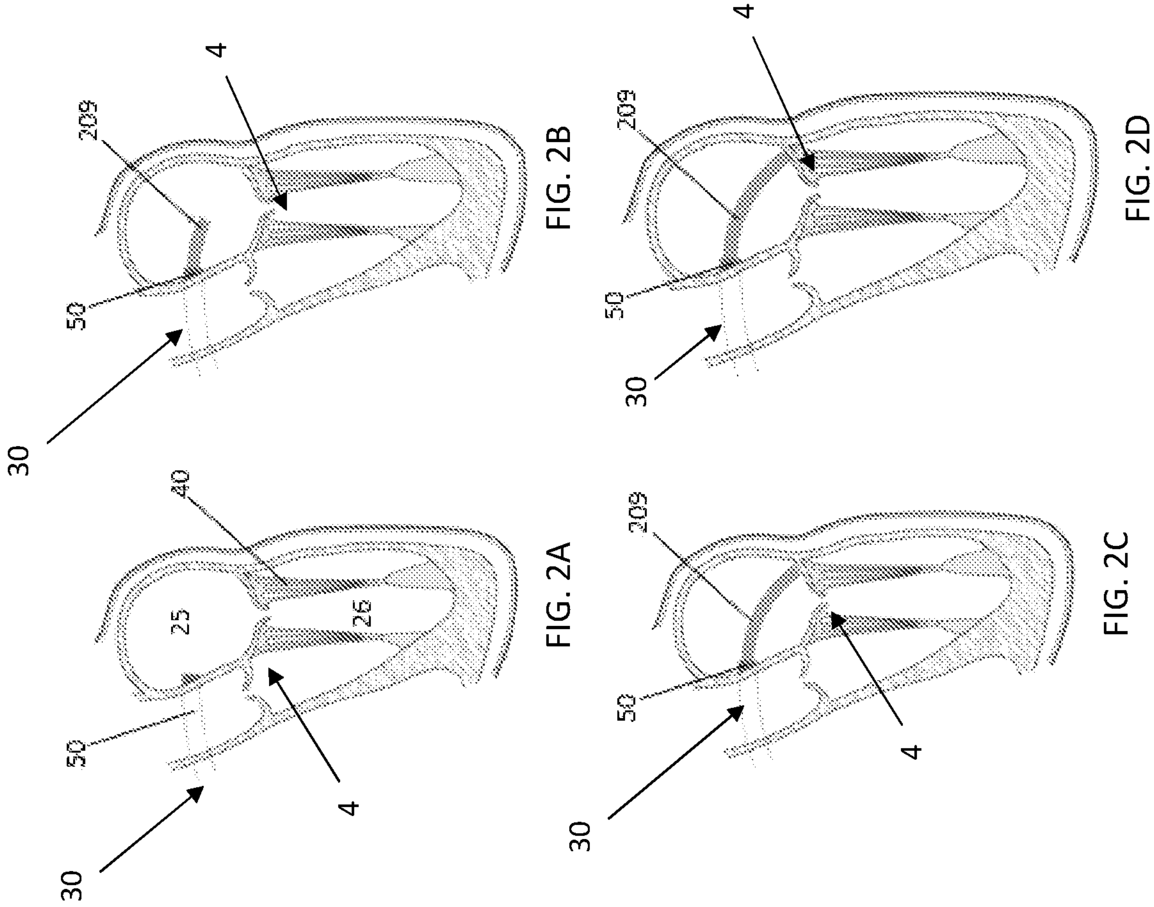
FIGS. 2A-2X show a series of diagrams outlining a method of positioning an anchor using an imaging source attached to the end of an anchor guidewire, in accordance with some embodiments.
Figures 2E, 2F, 2G:
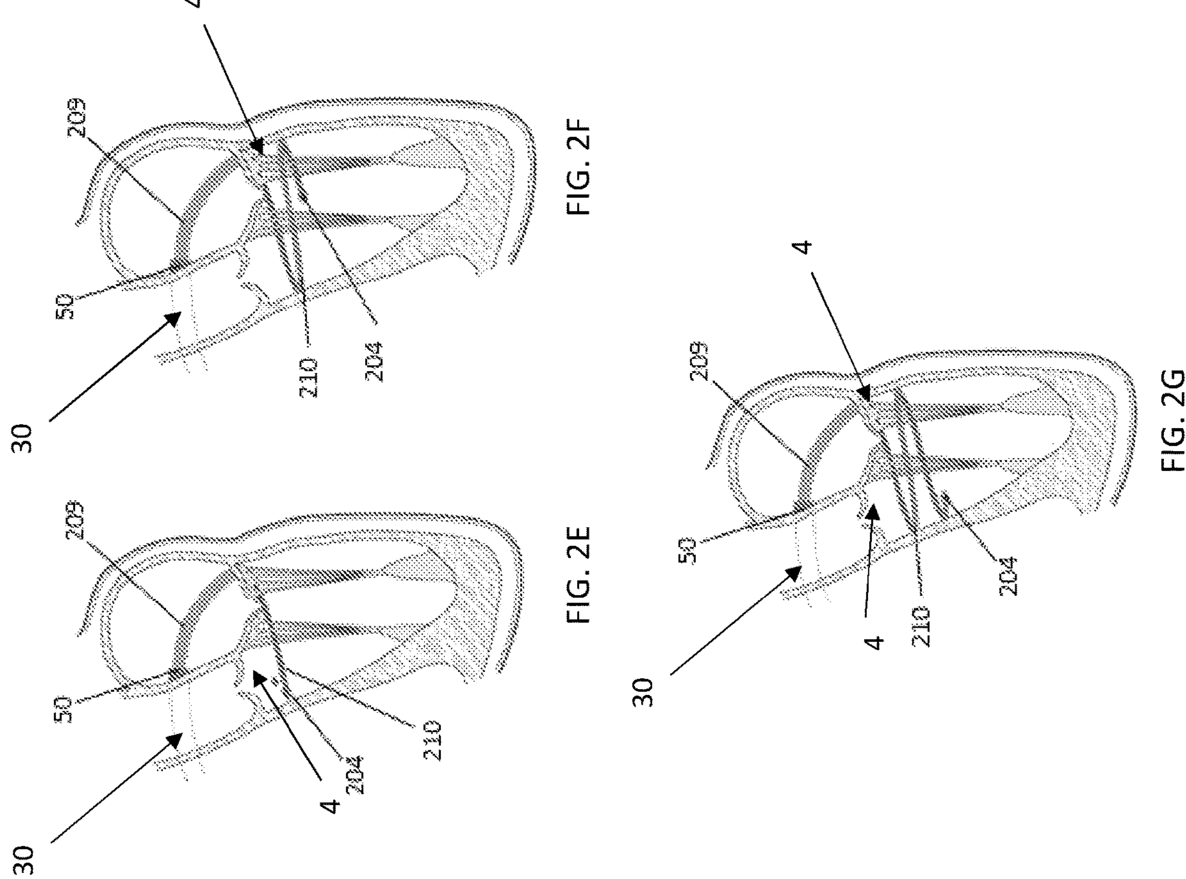
Figures 2H, 2I, 2J, 2K:
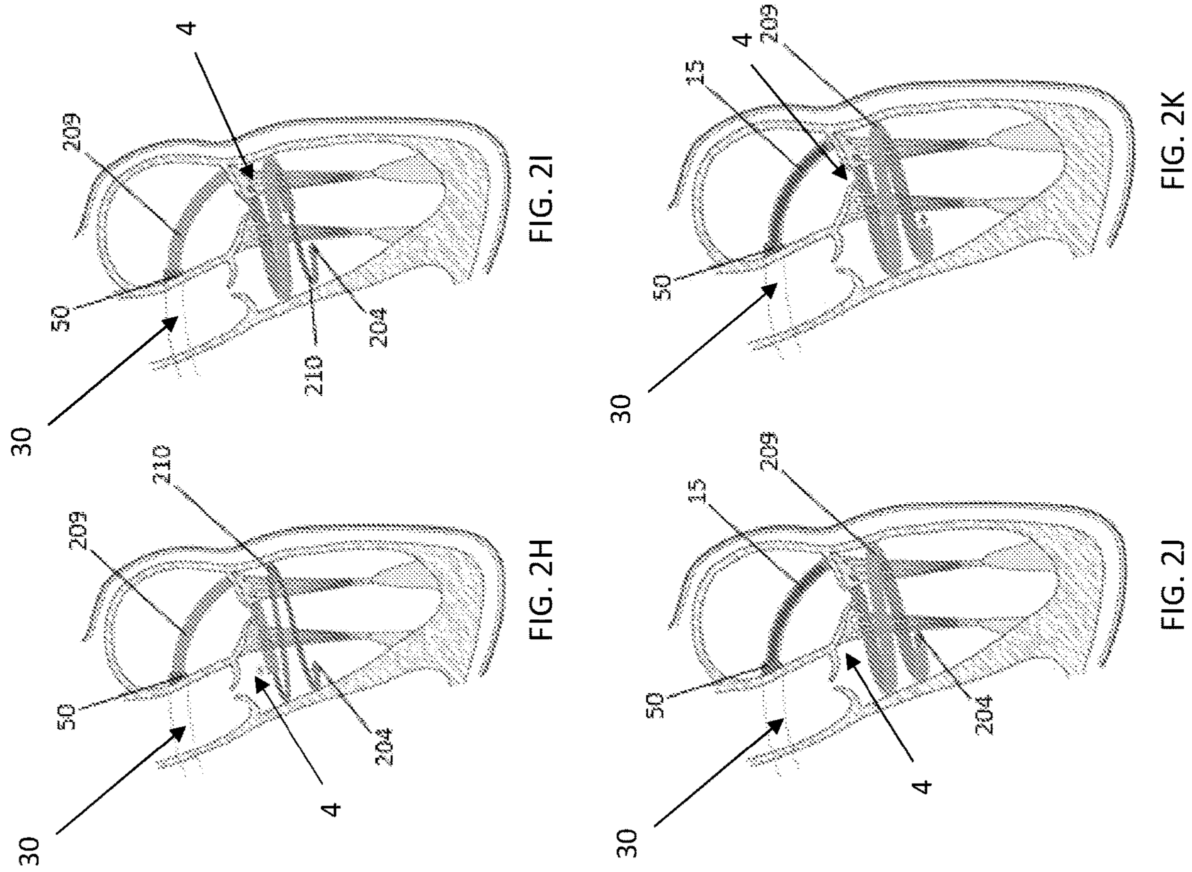
Figures 2L, 2M, 2N, 2O:
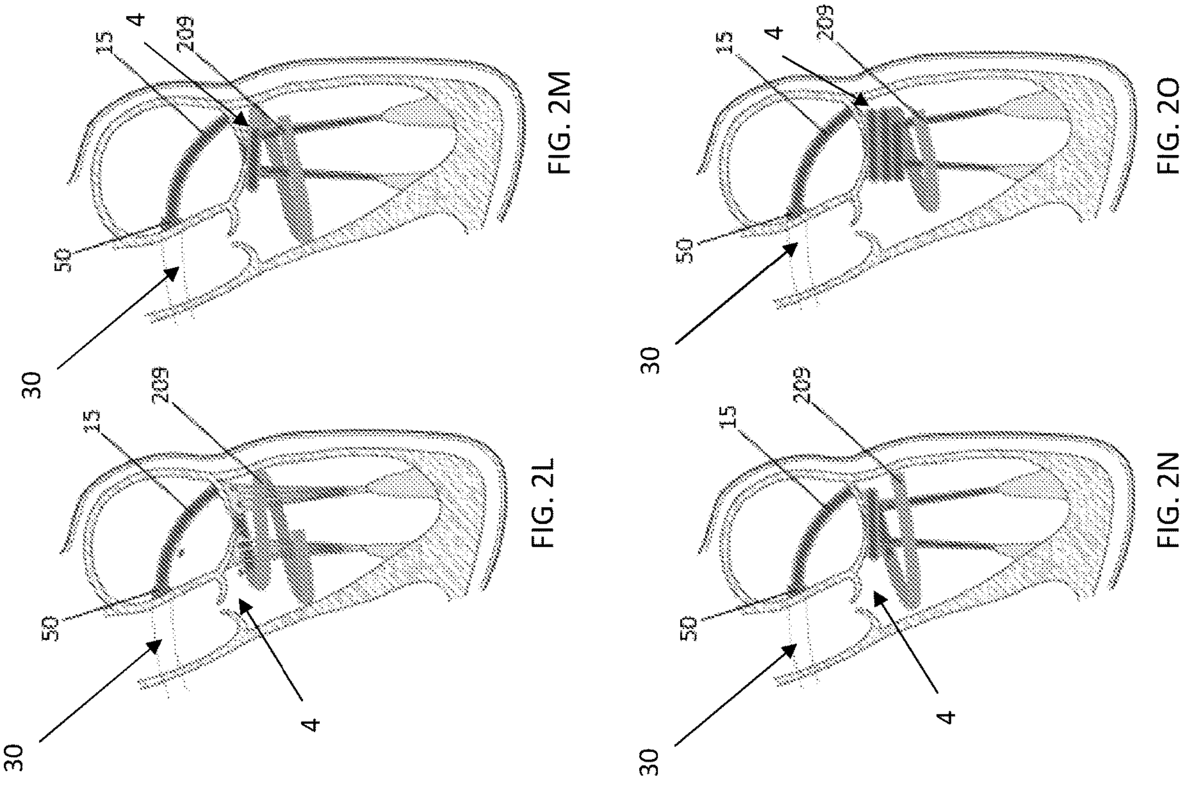
Figures 2P, 2Q, 2R:
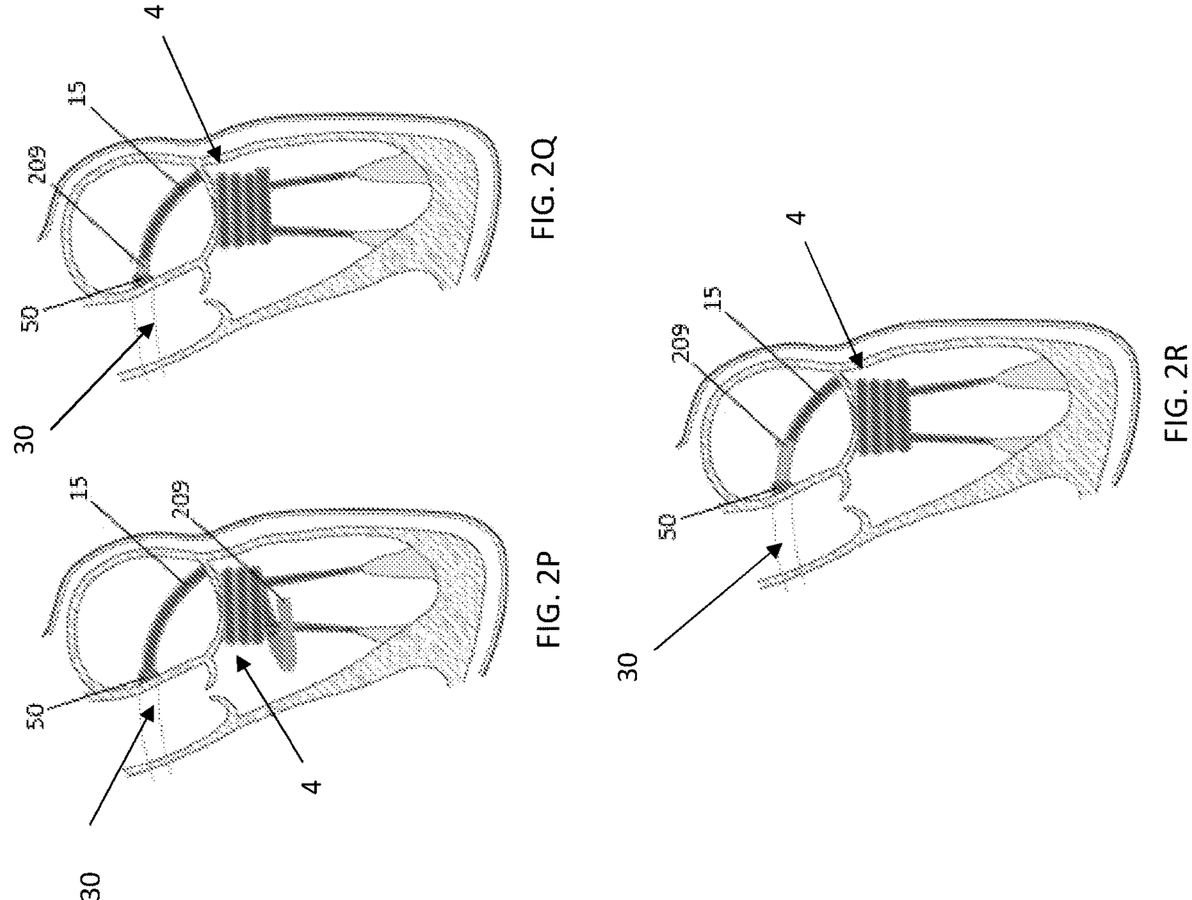
Figures 2S, 2T, 2U, 2V:
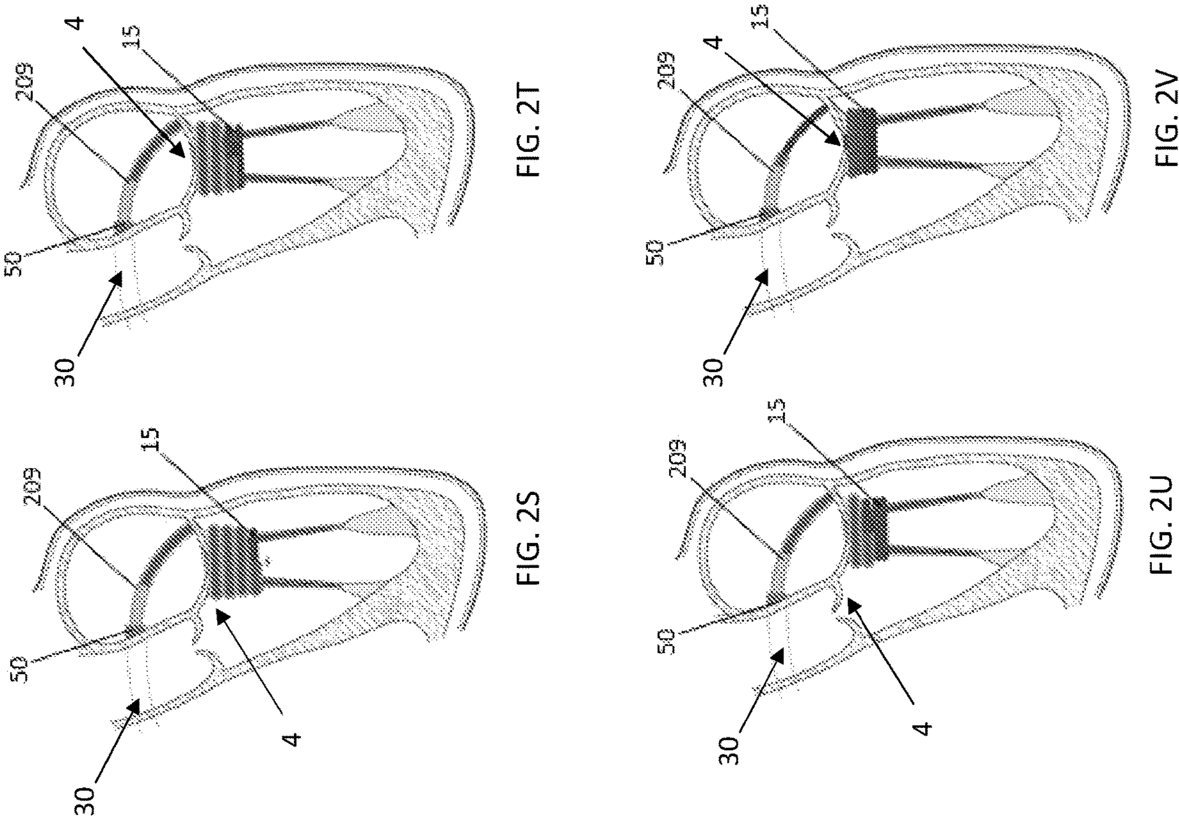
Figures 2W, 2X:
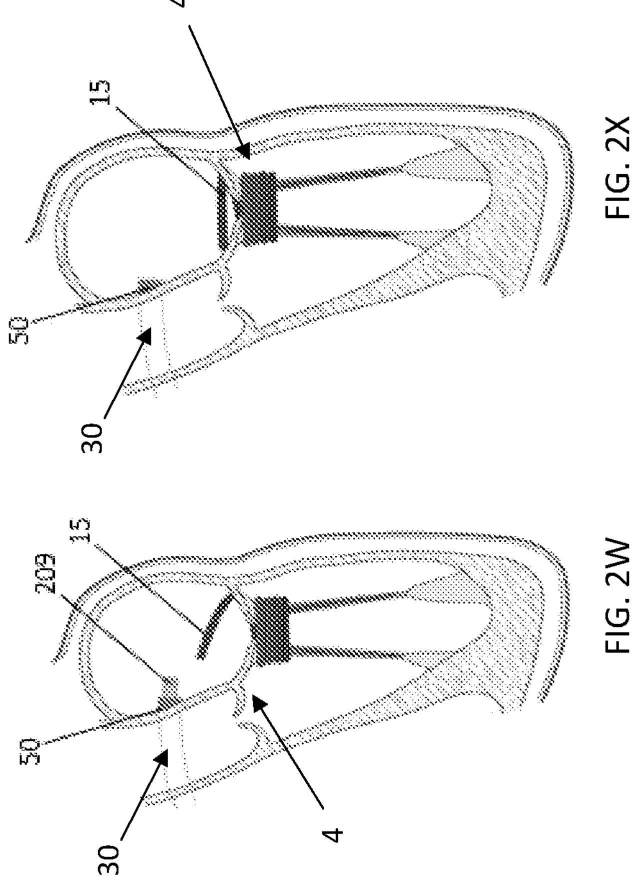

FIGS. 2A-2X show a method of placing an anchor 15 around native chordae tendineae 40 of a native heart valve 4 using an image capture device 204 mounted on the end of an anchor delivery guidewire 210 of a delivery device 30.

FIG. 2A shows the advancement of an outer sheath 50 of the delivery device 30 through a transseptal puncture. FIG. 2B shows the advancement of an anchor delivery sheath 209 of the delivery device 30 through the outer delivery sheath 50. FIGS. 2C-2D show the placement of the anchor delivery sheath 209 to an edge of the native heart valve 4.

FIGS. 2E-2G show the advancement of an anchor delivery guidewire 210 through the anchor delivery sheath 209 comprising the image capture device 204 on the distal end. In some embodiments, the image capture device 204 may be used to verify and confirm the proper positioning of the anchor delivery sheath 209 to the edge of the native heart valve 4. The anchor delivery sheath 209 may be re-positioned as guided by the images captured the image capture device 204. The image capture device 204 on the distal end of the anchor delivery guidewire 210 may additionally or alternatively guide capture of the chordae tendineae 40 by allowing the operator to visualize the chordae tendineae 40 and/or ventricular walls and direct the anchor delivery guidewire 210 in the appropriate direction. As shown in FIGS. 2E-2G, the anchor delivery guidewire 210 may be directed to encircle and capture the chordae tendineae 40. For example, the anchor delivery guidewire 210 may be guided by the image capture device 204 along the internal walls of the ventricle in order to ensnare the chordae tendineae 40.

FIGS. 2H-2J show the advancement of the anchor delivery sheath 209 over the anchor delivery guidewire 210. The anchor delivery sheath 209 may be directed by the anchor guidewire 210 to encircle and capture the chordae tendineae 40 as well.

FIG. 2K shows the retraction of the anchor delivery guidewire 210 through the anchor delivery sheath 209 after the anchor delivery sheath 209 has encircled the chordae tendineae 40.

FIGS. 2L-2R show the advancement of the anchor 15 through the anchor delivery sheath 209 after the anchor delivery guidewire 210 has been removed. In some embodiments, the anchor delivery guidewire 210 need not be removed before the anchor 15 is advanced. As the anchor 15 is advanced through the anchor delivery sheath 209, the anchor 15 may be guided by the anchor delivery sheath 209 to encircle the native chordae tendineae 40. The anchor 15 may have a stiffness greater than that of the anchor delivery sheath 209 such that, as the anchor 15 is advanced, the anchor 15 pulls the chordae tendineae 40 into tighter bunches than the anchor delivery sheath 209 alone.

Figure 3:
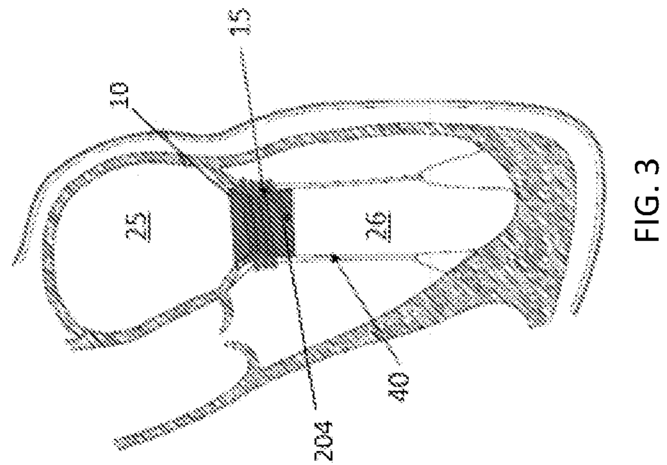
FIG. 3 is a section view of a valve prosthesis secured by an anchor at a diseased native valve, in accordance with some embodiments.

FIGS. 2S to 2X show the retraction of the anchor delivery sheath 209 from the fully advanced anchor 15, leaving the deployed anchor 15 around the native chordae tendineae 40. As shown in FIG. 3, once the anchor 15 is deployed around the native chordae tendineae 40, the prosthetic valve 10 may be expanded within the anchor 15. The anchor 15 may then be released from the distal end of the delivery device 30 (e.g., when the anchor is in the ventricle).

Advancing the anchor 15 may comprise pushing the anchor through the native valve 4. Advancing the anchor 15 may further comprise rotating the anchor 15 through the native valve 4. Advancing the anchor 15 within the anchor delivery sheath 209 may bring the captured chordae tendineae 40 closer in proximity to one another.

In some embodiments, the anchor 15 may be actuated from the delivery configuration to the deployed configuration on a first side of the native valve 4 prior to being advanced to a second side of the native valve 4. For example, the anchor 15 may be deployed in a left atrium of a heart prior to being advanced to a left ventricle of the heart as described herein.

Alternatively, the anchor 15 may be actuated from the delivery configuration to the deployed configuration on a second side of the native valve 4 after being advanced to the second side from a first side of the native valve 4. For example, anchor 15 may be advanced from a left atrium of a heart prior to being deployed in a left ventricle of the heart by the retreat of an outer sheath. An image capture device 204 can be used to verify and confirm the various steps of delivering and deploying the anchor. The image capture device 204 may be positioned in a variety of locations with respect to the anchor 15 and its associated delivery devices. The image capture device 204 may be located at a free end of the anchor 15 within a lumen of the anchor. The image capture device 204 may be located adjacent to the anchor 15.

The free end 22 of the deployed anchor 15 may optionally be rotated around one or more structures on the second side of the native valve 4. The free end 22 of the deployed anchor may include an image capture device 204 to aid in the placement of the anchor 15 around the native chordae tendineae 40. The one or more structures may comprise one or more valve leaflets 14 of the native valve 4. Alternatively, or in combination, the one or more structures may comprise one or more chordae 40 of the left ventricle. The free end of the deployed anchor 15 may optionally rotated around one or more structures on the second side of the native valve 4 such that the one or more structures (e.g., chordae, leaflets, or annulus) are pulled radially inwards towards the longitudinal axis of the anchor 15 and/or towards the longitudinal axis of the delivery device. The anchor 15 and/or free end may be configured such that minimal torque is applied to the one or more structures. Alternatively, or in combination, the anchor 15 and/or free end may be configured such that the one or more structures are not rotated, or are minimally rotated, during rotation of the anchor 15.

In some embodiments, fully deploying the anchor 15 may include positioning the anchor such that it is located only on the second side of the native valve 4.

In some embodiments, the anchor 15 may be actuated from the delivery configuration to the deployed configuration on a first side of the native valve 4 prior to being advanced to a second side of the native valve 4. For example, the anchor 15 may be deployed in a left atrium of a heart prior to being advanced to a left ventricle of the heart as described herein. In other embodiments, the anchor 15 may be actuated on the second side of the native valve.

Figures 4A, 4B, 4C:
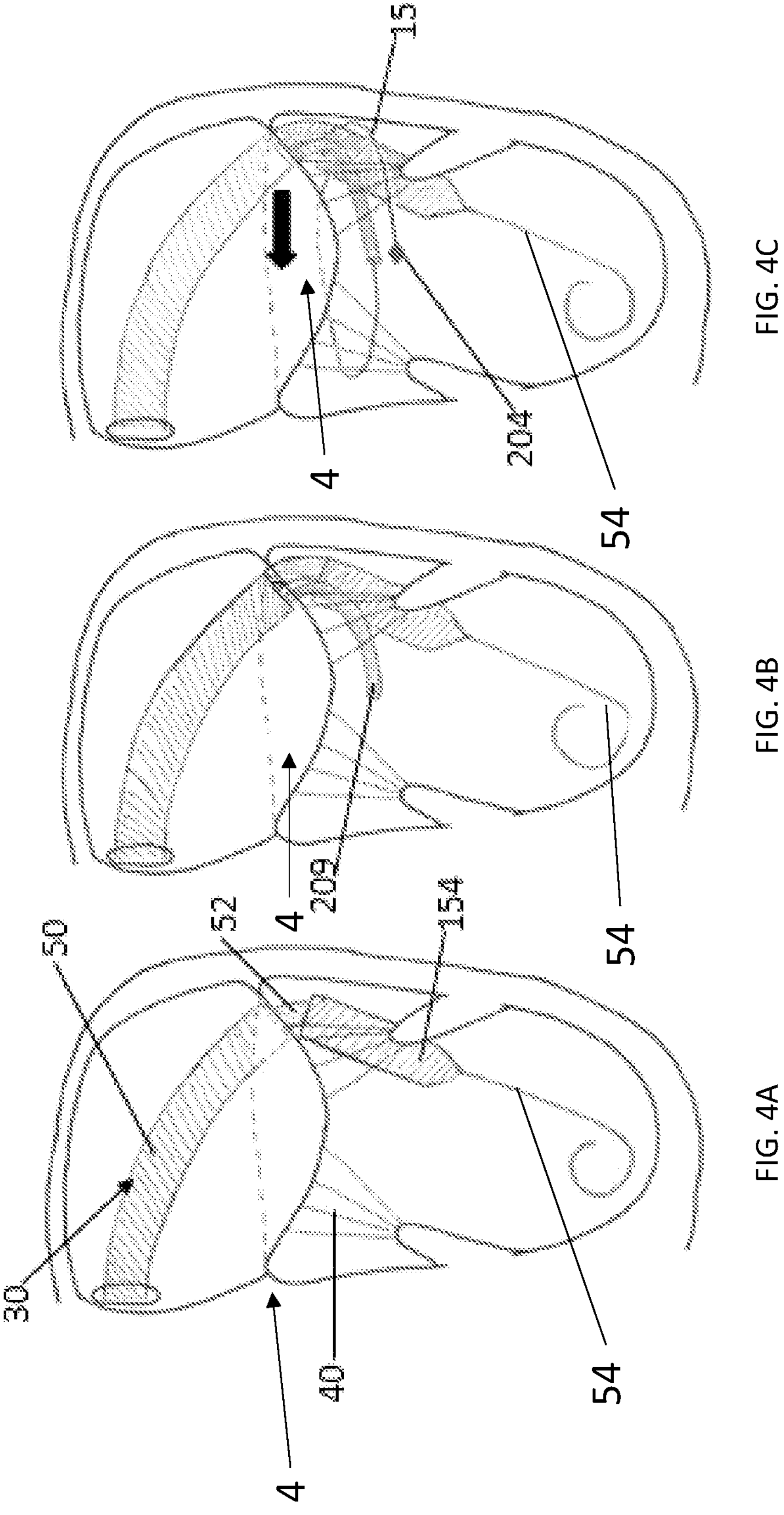
FIGS. 4A-4F shows a series of diagrams outlining a method of delivery of a valve prosthesis including an anchor having an image capture device attached to its distal end, in accordance with some embodiments.

FIGS. 4A-5 show a method of placing an anchor 15 around native chordae tendineae 40 of a native heart valve 4 using an image capture device 204 mounted on the distal end of the anchor 15. In this embodiment, the anchor 15 is shown as being actuated from the delivery configuration to the deployed configuration on a second side of the native valve 4 after being advanced to the second side from a first side of the native valve 4, though it should be understood that the method can be modified to deploy the anchor 15 in the first side of the native valve as described with respect to FIGS. 2A-2X.

As in the method described in FIGS. 2A-2X, the image capture device 204 may be used to guide, verify, and/or confirm the proper deployment of the anchor and valve prosthesis. FIG. 4A is a section view of a delivery device 30 which has been steered to an edge of the native valve 4 prior to deployment of the anchor 15. The delivery device 30 may be configured to be delivered into the heart over a guidewire 54 through a transseptal puncture in a manner substantially similar to that described herein (e.g., as shown in FIGS. 2A-2X). The delivery device 30 may include an outer sheath 50, a distal valve capsule 154, an inner shaft 52, and an anchor delivery sheath 209. The outer sheath 50 and/or distal valve capsule 154 may be steerable as described herein. The delivery device 30 may be steered through the native valve 4 such that the distal valve capsule 154 is positioned on below the native valve 4 and the outer sheath 50 is positioned above the native valve 4. Steering of the delivery device 30 may, in some embodiments, accomplished by a guidewire 54 with a deflection element, such as a rigid bend. The anchor delivery sheath 209 may also position the anchor 15 for attachment to the chordae tendineae 40 as described herein. A proximal pusher arm within the anchor delivery sheath 209 may position the anchor 15 for attachment to the chordae tendineae 40 as described herein.

FIG. 4B is a side section view of the delivery device 30 after the anchor delivery sheath 209 has been pushed through a lumen of the outer sheath 50 into the left ventricle. The opening formed by the separation of the outer sheath 50 and the distal valve capsule 154 may enable the anchor delivery sheath 209 to be delivered directly into the left ventricle. The anchor delivery sheath 209 may be substantially similar to any of the anchor delivery sheaths described herein.

FIG. 4C is a side section view of the delivery device 30 after the anchor 15 has been partially pushed through the anchor delivery sheath 209, thereby partially deploying the anchor 15 from the delivery conformation directly into the deployed conformation while simultaneously wrapping the anchor 15 around the native chordae tendineae 40. The anchor 15 may be pushed through the anchor delivery sheath 209 by a proximal pusher arm disposed within the lumen of the anchor delivery sheath 209, for example as described in U.S. patent application Ser. No. 16/824,576, filed on Mar. 19, 2020 titled, "PROSTHETIC CARDIAC VALVE DEVICES, SYSTEMS, AND METHODS," which is incorporated herein by reference. As shown in FIG. 4C, the anchor 15 can have an image capture device 204 on the distal end. The anchor 15 may be guided via aid from the image capture device 204 on the distal end of the anchor 15. For example, the image capture device 204 may aid in steering the anchor 15 as it is released from the radial constriction of the anchor delivery sheath 209.

Figures 4D, 4E, 4F:
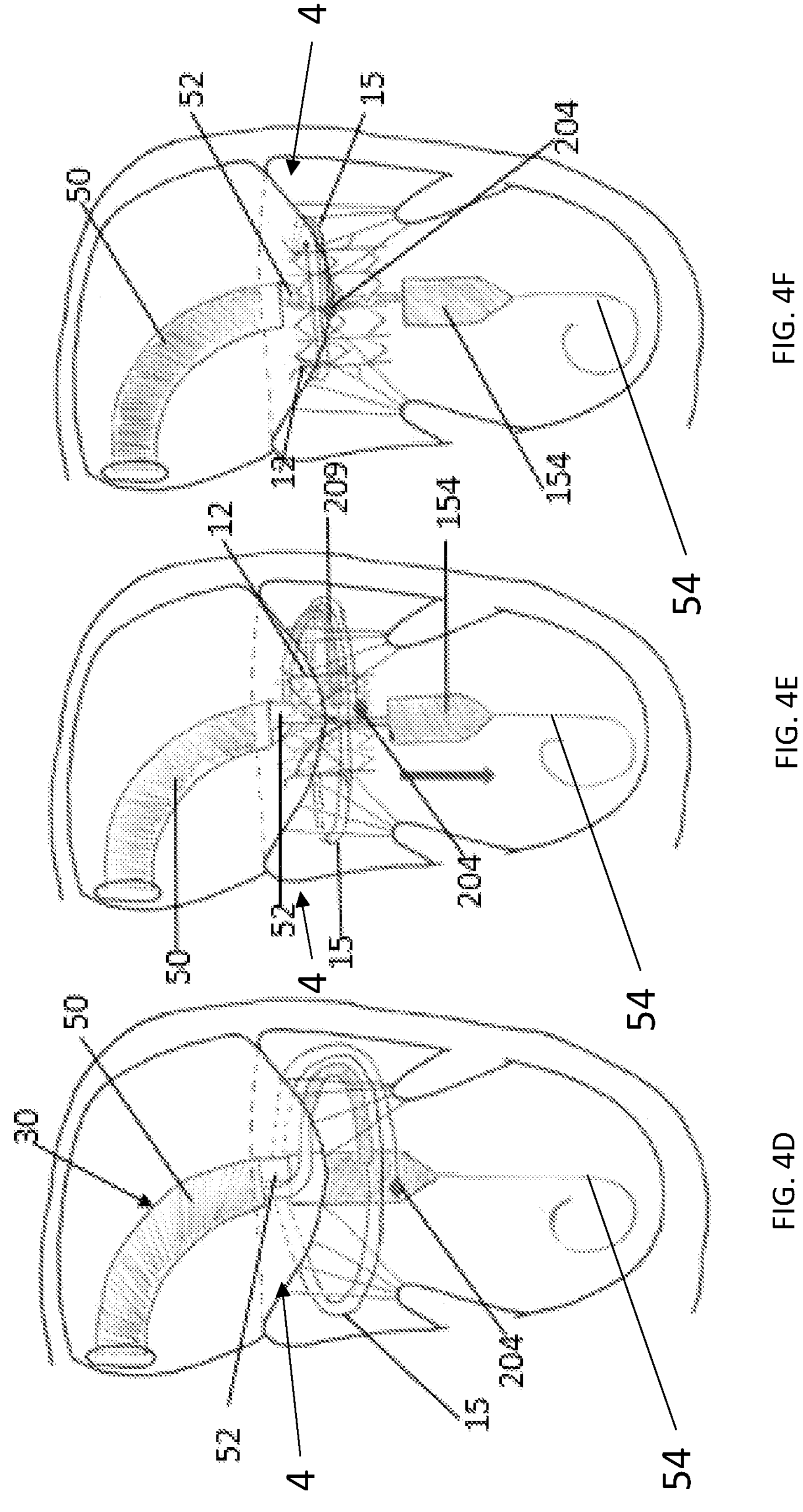

FIG. 4D is a section view of the repositioning of the delivery device 30 to the center of the diseased native valve 4 and the continued deployment of the anchor 15 from the anchor delivery sheath 209. The anchor 15 may be wrapped around one or more structures of the native valve (e.g., chordae tendineae), as described herein. For example, direct deployment of the anchor 15 from the anchor delivery sheath 209 in the left ventricle may facilitate wrapping as the anchor 15 transitions from the delivery configuration to the deployed configuration. Alternatively, or in combination, the anchor 15 may be rotated during or after deployment as described herein.

FIG. 4E is a section views of the deployment of the frame structure 12 of the valve prosthesis 10 from an opening created by the separation of the distal end of the distal valve capsule 154 from the outer sheath 50. The frame structure 12 may be expanded from an unexpanded configuration to an expanded configuration as described herein. In some embodiments, separation of the distal end of the outer sheath assembly 154 from the outer sheath 50 may be facilitated by the advancement of an inner shaft 52 through the lumen of the outer sheath 50 such that the distal valve capsule 154 is pushed away from the outer sheath 50 by the inner shaft 52. The frame structure 12 can be maintained in the delivery configuration by radial constriction from one or more of the distal valve capsule 154 or the outer sheath 50.

The anchor 15 may be detachably coupled to a proximal or distal portion of the frame structure 12 as described herein. Alternatively or in combination, the frame structure 12 may be detachably coupled to the delivery device 30 in the delivery configuration during delivery to the native valve 4. For example, the proximal end of the frame structure 12 may be detachably coupled to the inner shaft 52 of the delivery device 30 by radial constriction from the outer sheath 50 or the distal end of the outer sheath assembly 154. Retraction of the outer sheath 50 away from the proximal end of the frame structure 12 (or, similarly, extrusion of the distal end of the frame structure 12 out of an opening in the outer sheath) may detach the frame structure 12 from the delivery device 30. Alternatively, or in combination, the proximal end of the frame structure 12 may be detachably coupled to the inner shaft 52 of the delivery device 30 by an attachment element. Alternatively, or in combination, the proximal end of the frame structure may be detachably coupled to the inner shaft 52 of the delivery device 30 by a weak adhesive.

FIG. 4F is a section view showing the final position of the valve prosthesis 10 following retraction of the anchor delivery sheath 209. The anchor 15 may be wrapped around the native chordae tendineae 40 in order to lock the valve prosthesis 10 in place as described herein. The frame structure 12 may be released from the delivery device 30 as described herein. The delivery device 30 may then be retracted to leave the cardiac valve device in place (e.g., as shown in FIG. 5). The cardiac valve device may allow blood to flow from the left atrium 25 to the left ventricle 26 while preventing backflow or regurgitation in the reverse direction.

FIGS. 6A-6D show a method of placing an anchor 15 around native chordae tendineae 40 of a native heart valve 4 using an image capture device 240 that includes a plurality of sensors 241 mounted along a length of the anchor 15. Like the method of FIGS. 2A-2X and FIGS. 4A-5, the image capture device 240 can be used to guide, verify, and/or confirm the proper deployment of the anchor and valve prosthesis.

Figure 6A:
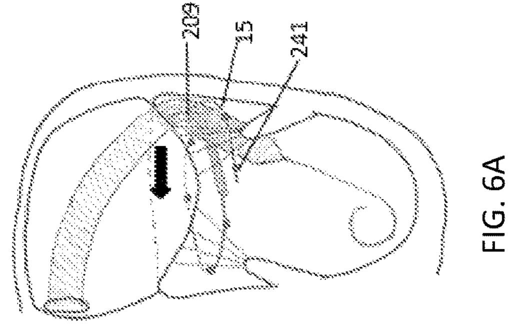
FIGS. 6A-6D show a series of diagrams outlining a method of delivery of a valve prosthesis include an anchor having a series of sensors disposed along the length of the anchor, in accordance with some embodiments.

FIG. 6A is a side section view of the delivery device 30 after the anchor 15 has been partially pushed through the anchor delivery sheath 209, thereby partially deploying the anchor 15 from the delivery conformation directly into the deployed conformation while simultaneously wrapping the anchor 15 around the native chordae tendineae 40. The anchor 15 may be pushed through the anchor delivery sheath 209 by a proximal pusher arm disposed within the lumen of the anchor delivery sheath 209, for example as described in U.S. patent application Ser. No. 16/824,576, filed on Mar. 19, 2020, previously incorporated herein by reference. The anchor 15 may be guided via aid from the series of sensors 241 located along the length of the anchor 15 as described herein. Information gathered from each sensor 241 may be relayed to a user to indicate contact with the chordae tendineae 40 as described herein.

Figure 6B:
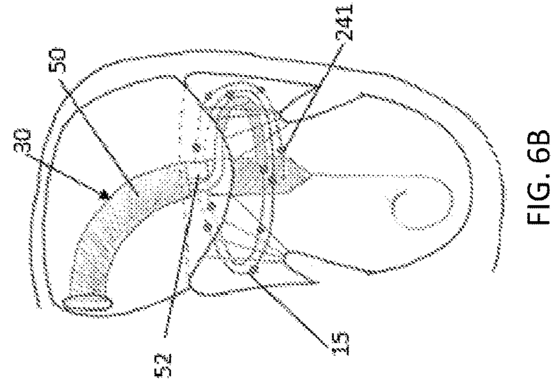

FIG. 6B shows a section view of the repositioning of the delivery device 30 to the center of the diseased valve and the continued deployment of the anchor 15 from the anchor delivery sheath 209. The anchor 15 may be wrapped around one or more structures of the native valve (e.g., chordae tendineae), as described herein. For example, the anchor 15 may be rotated during or after deployment as described herein. The anchor 15 may be guided via aid from the series of sensors 241 located along the length of the anchor 15 as described herein. Information gathered from each sensor 241 may be relayed to a user to indicate contact with the chordae tendineae 40.

Figure 6C:
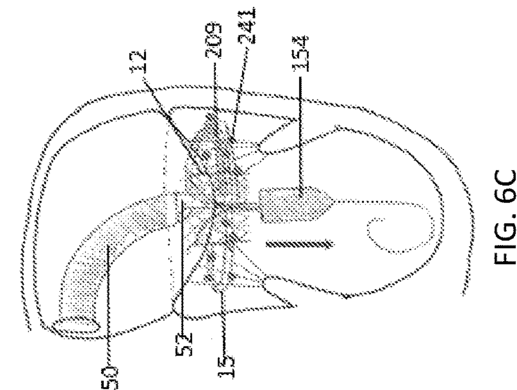

FIG. 6C is a section views of the deployment of the frame structure 12 of the valve prosthesis 10 from an opening created by the separation of the distal valve capsule 154 from the outer sheath 50. The frame structure 12 may be expanded from an unexpanded configuration to an expanded configuration as described herein. The frame structure 12 can be maintained in the delivery configuration by radial constriction from one or more of the distal end of the outer sheath assembly 154 or the outer sheath 50 as described herein.

Figure 6D:
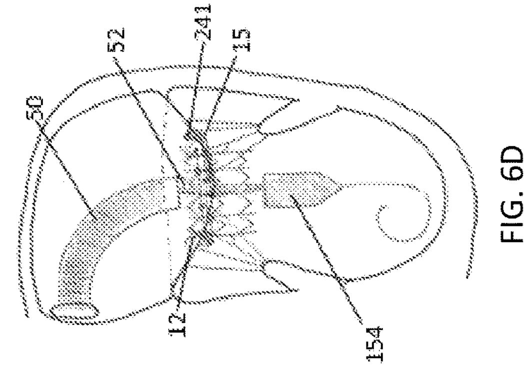

FIG. 6D is a section view showing the final position of the valve prosthesis 10 following retraction of the anchor delivery sheath 209. The anchor 15 may be wrapped around the native chordae tendineae 40 in order to lock the valve prosthesis 10 in place as described herein. The frame structure 12 may be released from the delivery device 30 as described herein. The delivery device 30 may then be retracted to leave the valve prosthesis 10 in place (e.g., as shown in FIG. 5).

In some embodiments, the anchor 15 may include a wire or band. In some embodiments, the anchor 15 may include a coiled wire or band, a helical wire or band, or a spiral wire or band in the deployed configuration. In various embodiments, the wire or band may have a coiled, helical, or spiral shape in the deployed configuration. In various embodiments, the wire or band may be elongated, rather than coil/helical/spiral-shaped—in the delivery configuration. In various embodiments, a portion of the wire or band may have a coiled, helical, or spiral shape.

The anchor 15 may include a lumen through which the image capture device 240 and/or wiring is threaded to be placed at a distal end of the anchor 15. Alternatively, or in combination, the image capture device 240 may be disposed adjacent the anchor 15 within the same or a different lumen of the delivery device 30. In some embodiments, an elongated image capture device 204 may be translatably disposed within the lumen. The translatable image capture device 204 may be translated adjacent the distal end of the anchor 15 during imaging and, after imaging, may be removed from the anchor 15 and the body or left within the lumen following deployment.

Although the image capture device 240 is described as being part of (e.g., attached to or positioned within) an anchor 15 or delivery device 30, it is to be understood that additional or alternative imaging sources may be used. For example, in some embodiments, the imaging source can include a radiographic imaging system (such as a fluoroscopy system) which may be used to guide and/or monitor deployment of the valve prosthesis. In some embodiments, the fluoroscopy system can include an X-ray image intensifier. In some embodiments, the fluoroscopy system can include a flat-panel detector. In some embodiments, the anchor 15 and/or the frame structure 12 may comprise a radiopaque element or a material to allow the anchor 15 and/or frame structure 12 to be visualized using fluoroscopy. In some embodiments, the image capture device 204 (e.g., sensors 241 along the length of the anchor), described herein, can further comprise one or more radiopaque elements. The radiopaque element may be disposed on a distal end of the anchor 15. The radiopaque element may comprise a metal tip or a plastic tip with a radiopaque element such as barium, iodine, or the like as will be understood by one of ordinary skill in the art based on the teachings herein.

Further, although described in terms of an image capture device 204, one will appreciate from the description herein that sensors other than for imaging may alternatively or additionally be used. In various respects, "sensor" or "capture device" is used somewhat generally to refer to any such modalities including, but not limited to, imaging modalities and sensors for detecting pressure, temperature, strain or deflection, and the like. In various embodiments, the anchor 15 can include multiple imaging and/or sensing modalities. These modalities may be at the distal end of the anchor 15, at the tip, or anywhere along the length of the anchor 15 or the delivery device 30. In various embodiments, the anchor 15 may include such modalities at the free end and the proximal end such that the clinician can confirm deployment (when the anchor 15 is fully unsheathed) and monitor encircling of the chordae and papillary muscles.

It should be understood that any feature described herein with respect to one embodiment can be used in addition to or in place of any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A prosthetic cardiac valve device for treating a diseased native valve of a heart, the device comprising:

a frame structure having a compressed configuration and an expanded configuration;

a spiral anchor configured to be positioned around the frame structure, the spiral anchor configured to anchor the frame structure to the native valve; and an image capture device comprising a camera, the image capture device attached to or positioned within the spiral anchor and configured to confirm placement of the spiral anchor within the heart.

2. The device of claim 1, wherein the spiral anchor is configured to be fully advanced in the expanded configuration from an atrium of the heart through the native valve and into a ventricle of the heart.

3. The device of claim 1, wherein the camera is disposed within an inflatable membrane filled with an inflation fluid.

4. The device of claim 3, wherein the membrane is porous.

5. The device of claim 4, wherein the membrane is configured to diffuse saline therethrough.

6. The device of claim 1, wherein the image capture device is coupled to an external surface of the spiral anchor.

7. The device of claim 1, wherein the image capture device is positioned within a central lumen of the spiral anchor.

8. The device of claim 1, wherein the image capture device is coupled to a distal free end of the spiral anchor.

9. The device of claim 1, wherein image capture device comprises a plurality of sensors disposed along a length of the spiral anchor.

10. The device of claim 9, wherein the plurality of sensors comprise an impedance sensor.

11. The device of claim 9, wherein the plurality of sensors comprise a pressure sensor.

12. The device of claim 9, wherein the plurality of sensors comprise a radiopaque element.

13. The device of claim 1, wherein a distal free end of the spiral wire is configured to extend radially outward from a circumference of the spiral wire when the spiral wire is positioned around the frame structure.

14. The device of claim 1, wherein the frame structure is configured to expand within the native valve.

15. The device of claim 1, wherein the compressed configuration is sized and dimensioned for percutaneous insertion and the expanded configuration is sized and dimensioned for implantation in the native valve.

16. The device of claim 1, wherein the frame structure comprises a first and second opposite ends, the first end configured to extend above the native valve and the second end configured to extend below the native valve when the frame structure is anchored to the native valve.

* * * * *